(12) United States Patent
MacEwan

(10) Patent No.: US 11,224,677 B2
(45) Date of Patent: *Jan. 18, 2022

(54) TISSUE SUBSTITUTE MATERIALS AND METHODS FOR TISSUE REPAIR

(71) Applicant: Acera Surgical, Inc., St. Louis, MO (US)

(72) Inventor: Matthew MacEwan, St. Louis, MO (US)

(73) Assignee: Acera Surgical, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/226,384

(22) Filed: Apr. 9, 2021

(65) Prior Publication Data

US 2021/0236691 A1 Aug. 5, 2021

Related U.S. Application Data

(63) Continuation of application No. 16/816,084, filed on Mar. 11, 2020, which is a continuation of application No. 15/152,726, filed on May 12, 2016, now Pat. No. 10,632,228.

(51) Int. Cl.
*A61L 27/18* (2006.01)
*A61L 27/26* (2006.01)
*A61L 27/58* (2006.01)

(52) U.S. Cl.
CPC ............... *A61L 27/18* (2013.01); *A61L 27/26* (2013.01); *A61L 27/58* (2013.01); *A61L 2430/32* (2013.01)

(58) Field of Classification Search
USPC ................. 623/23.72; 427/2.31; 264/466
See application file for complete search history.

(56) References Cited

U.S. PATENT DOCUMENTS

| 2,068,703 A | 1/1937 | Powdermaker |
| 3,280,229 A | 10/1966 | Simons |
| 3,338,992 A | 8/1967 | Kinney |

(Continued)

FOREIGN PATENT DOCUMENTS

| AU | 2011268321 | 1/2013 |
| AU | 2012390291 | 9/2017 |

(Continued)

OTHER PUBLICATIONS

3rd International Conference on Electrospinning Conference Program dated Aug. 4-7, 2004, www.ceramics.org/electrospin2014.

(Continued)

*Primary Examiner* — Lynda Salvatore
(74) *Attorney, Agent, or Firm* — Knobbe, Martens, Olson & Bear, LLP

(57) ABSTRACT

Non-woven graft materials for use in specialized surgical procedures such as neurosurgical procedures, methods for making the non-woven graft materials, and methods for repairing tissue such as neurological tissue using the non-woven graft materials are disclosed. More particularly, disclosed are non-woven graft materials including at least two distinct fiber compositions composed of different polymeric materials, methods for making the non-woven graft materials and methods for repairing tissue in an individual in need thereof using the non-woven graft materials.

30 Claims, 8 Drawing Sheets

(56) References Cited

U.S. PATENT DOCUMENTS

| | | |
|---|---|---|
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,740,302 A | 6/1973 | Soehngen |
| 3,802,817 A | 4/1974 | Matsuki |
| 3,849,241 A | 11/1974 | Butin et al. |
| 3,909,009 A | 9/1975 | Cvetko et al. |
| 4,044,404 A | 8/1977 | Martin et al. |
| 4,340,563 A | 7/1982 | Appel et al. |
| 4,468,428 A | 8/1984 | Early et al. |
| 4,738,740 A | 4/1988 | Pinchuk et al. |
| 4,965,110 A | 10/1990 | Berry |
| 5,024,789 A | 6/1991 | Berry |
| 5,079,080 A | 1/1992 | Schwarz |
| 5,306,550 A | 4/1994 | Nishiyama et al. |
| 5,464,450 A | 11/1995 | Buscemi et al. |
| 5,591,335 A | 1/1997 | Barboza et al. |
| 5,626,611 A | 5/1997 | Liu et al. |
| 5,795,584 A | 8/1998 | Totakura et al. |
| 5,851,937 A | 12/1998 | Wu et al. |
| 5,997,568 A | 12/1999 | Liu |
| 6,147,135 A | 11/2000 | Yuan et al. |
| 6,162,535 A | 12/2000 | Turkevich et al. |
| 6,171,338 B1 | 1/2001 | Talja et al. |
| 6,180,848 B1 | 1/2001 | Flament et al. |
| 6,183,670 B1 | 2/2001 | Torobin et al. |
| 6,265,333 B1 | 7/2001 | Dzenis et al. |
| 6,306,424 B1 | 10/2001 | Vyakarnam et al. |
| 6,391,060 B1 | 5/2002 | Ory et al. |
| 6,596,296 B1 | 7/2003 | Nelson et al. |
| 6,630,231 B2 | 10/2003 | Perez et al. |
| 6,649,807 B2 | 11/2003 | Mizutani |
| 6,685,956 B2 | 2/2004 | Chu et al. |
| 6,689,374 B2 | 2/2004 | Chu et al. |
| 6,713,011 B2 | 3/2004 | Chu et al. |
| 6,753,454 B1 | 6/2004 | Smith et al. |
| 6,790,455 B2 | 9/2004 | Chu et al. |
| 6,797,655 B2 | 9/2004 | Rudisill |
| 6,946,506 B2 | 9/2005 | Bond et al. |
| 7,134,857 B2 | 11/2006 | Andrady et al. |
| 7,172,765 B2 | 2/2007 | Chu et al. |
| 7,192,604 B2 | 3/2007 | Brown et al. |
| 7,655,070 B1 | 2/2010 | Dallas et al. |
| 7,759,082 B2 | 7/2010 | Bowlin et al. |
| 7,799,262 B1 | 9/2010 | Kim |
| 7,846,466 B2 | 12/2010 | Shea et al. |
| 7,879,093 B2 | 2/2011 | Wei et al. |
| 7,981,353 B2 | 7/2011 | Mitchell et al. |
| 8,066,932 B2 | 11/2011 | Xu |
| 8,222,166 B2 | 7/2012 | Chu et al. |
| 8,273,369 B2 * | 9/2012 | Moloye-Olabisi ...... A61L 15/44 424/444 |
| 8,652,215 B2 | 2/2014 | Bellamkonda et al. |
| 8,728,463 B2 | 5/2014 | Atala et al. |
| 8,728,817 B2 | 5/2014 | Ogle et al. |
| 8,809,212 B1 | 8/2014 | Dirk et al. |
| 8,852,621 B2 | 10/2014 | Patel |
| 9,074,172 B2 | 7/2015 | Johnson |
| 9,085,830 B2 | 7/2015 | Mitchell et al. |
| 9,163,331 B2 | 10/2015 | Atala et al. |
| 9,168,231 B2 | 10/2015 | Patel et al. |
| 9,345,486 B2 | 5/2016 | Zhang et al. |
| 9,393,097 B2 | 7/2016 | McCullen et al. |
| 9,476,026 B2 | 10/2016 | Arinzeh et al. |
| 9,487,893 B2 * | 11/2016 | Moore ...................... D01F 1/10 |
| 9,539,365 B2 | 1/2017 | Kasunga et al. |
| 9,572,909 B2 | 2/2017 | Simpson et al. |
| 9,585,666 B2 | 3/2017 | Yu et al. |
| 9,737,632 B2 | 8/2017 | Johnson et al. |
| 9,884,027 B2 | 2/2018 | Johnson |
| 9,938,373 B2 | 4/2018 | Wang et al. |
| 10,016,464 B2 | 7/2018 | Murphy et al. |
| 10,080,687 B2 | 9/2018 | MacEwan |
| 10,124,089 B2 | 11/2018 | MacEwan |
| 10,149,749 B2 | 12/2018 | MacEwan et al. |
| 10,166,315 B2 | 1/2019 | Johnson et al. |
| 10,227,568 B2 | 3/2019 | Johnson |
| 10,231,821 B2 | 3/2019 | Gabriele et al. |
| 10,233,427 B2 | 3/2019 | Johnson |
| 10,239,262 B2 | 3/2019 | Johnson |
| 10,294,449 B2 | 5/2019 | Johnson |
| 10,335,154 B2 | 7/2019 | Johnson et al. |
| 10,363,041 B2 | 7/2019 | Yu et al. |
| 10,381,672 B2 | 8/2019 | Lee et al. |
| 10,405,963 B2 | 9/2019 | McAlpine et al. |
| 10,406,346 B2 | 9/2019 | Scott-Carnell et al. |
| 10,413,574 B2 | 9/2019 | Fong et al. |
| 10,420,856 B2 | 9/2019 | Arinzeh et al. |
| 10,441,403 B1 | 10/2019 | MacEwan et al. |
| 10,441,685 B2 | 10/2019 | MacEwan |
| 10,588,734 B2 | 3/2020 | MacEwan et al. |
| 10,617,512 B2 | 4/2020 | MacEwan |
| 10,632,228 B2 * | 4/2020 | MacEwan ............... A61L 27/18 |
| 10,682,444 B2 | 6/2020 | MacEwan |
| 10,738,152 B2 | 8/2020 | Wang et al. |
| 10,888,409 B2 | 1/2021 | MacEwan |
| 11,000,358 B2 | 5/2021 | MacEwan |
| 11,096,772 B1 | 8/2021 | MacEwan et al. |
| 11,176,234 B2 | 11/2021 | MacEwan et al. |
| 2002/0081732 A1 | 6/2002 | Bowlin et al. |
| 2002/0090725 A1 | 7/2002 | Simpson et al. |
| 2002/0173213 A1 | 11/2002 | Chu et al. |
| 2002/0192251 A1 | 12/2002 | Collin |
| 2003/0004579 A1 | 1/2003 | Rousseau et al. |
| 2003/0054035 A1 | 3/2003 | Chu et al. |
| 2004/0013819 A1 | 1/2004 | Hou et al. |
| 2004/0018226 A1 | 1/2004 | Wnek et al. |
| 2004/0037813 A1 | 2/2004 | Simpson et al. |
| 2004/0096532 A1 | 5/2004 | Dubson et al. |
| 2004/0102614 A1 | 5/2004 | Islam et al. |
| 2005/0104258 A1 | 5/2005 | Lennhoff |
| 2005/0167311 A1 | 8/2005 | Tonsfeldt et al. |
| 2005/0222591 A1 | 10/2005 | Gingras et al. |
| 2006/0014460 A1 | 1/2006 | Alexander Isele et al. |
| 2006/0085063 A1 | 4/2006 | Shastri et al. |
| 2006/0094320 A1 | 5/2006 | Chen et al. |
| 2006/0153904 A1 | 7/2006 | Smith et al. |
| 2006/0193578 A1 | 8/2006 | Ouderkirk et al. |
| 2006/0204539 A1 | 9/2006 | Atala et al. |
| 2006/0240110 A1 | 10/2006 | Kiick et al. |
| 2006/0246798 A1 | 11/2006 | Reneker et al. |
| 2006/0263417 A1 | 11/2006 | Lelkes et al. |
| 2006/0264140 A1 | 11/2006 | Andrady |
| 2007/0073344 A1 | 3/2007 | Jahns et al. |
| 2007/0152378 A1 | 7/2007 | Kim |
| 2007/0155273 A1 | 7/2007 | Chu et al. |
| 2007/0225631 A1 | 9/2007 | Bowlin et al. |
| 2007/0269481 A1 | 11/2007 | Li et al. |
| 2008/0065123 A1 | 3/2008 | Yli-Urpo et al. |
| 2008/0112998 A1 | 5/2008 | Wang |
| 2008/0207798 A1 | 8/2008 | Hellring et al. |
| 2008/0208358 A1 | 8/2008 | Bellamkoda et al. |
| 2008/0220042 A1 | 9/2008 | Hashi et al. |
| 2008/0237934 A1 | 10/2008 | Reneker et al. |
| 2009/0028921 A1 | 1/2009 | Arinzeh |
| 2009/0075354 A1 | 3/2009 | Reneker et al. |
| 2009/0074832 A1 | 5/2009 | Zussman et al. |
| 2009/0155326 A1 | 6/2009 | Mack et al. |
| 2009/0162468 A1 | 6/2009 | Barinov et al. |
| 2009/0171467 A1 | 7/2009 | Mann et al. |
| 2009/0202616 A1 | 8/2009 | Chong et al. |
| 2009/0214614 A1 | 8/2009 | Everland et al. |
| 2009/0228021 A1 | 9/2009 | Leung |
| 2009/0317446 A1 | 12/2009 | Tan et al. |
| 2010/0003305 A1 | 1/2010 | Pattanaik |
| 2010/0047309 A1 | 2/2010 | Lu et al. |
| 2010/0061962 A1 | 3/2010 | Li |
| 2010/0076377 A1 | 3/2010 | Ehrenreich et al. |
| 2010/0092687 A1 | 4/2010 | Sumida et al. |
| 2010/0093093 A1 | 4/2010 | Leong et al. |
| 2010/0119564 A1 | 5/2010 | Kasuga et al. |
| 2010/0120115 A1 | 5/2010 | Ogle et al. |
| 2010/0166854 A1 | 7/2010 | Michniak-Kohn et al. |

(56) References Cited

U.S. PATENT DOCUMENTS

| | | |
|---|---|---|
| 2010/0174368 A1 | 7/2010 | Lynch et al. |
| 2010/0179659 A1 | 7/2010 | Li et al. |
| 2010/0185219 A1 | 7/2010 | Gertzman et al. |
| 2010/0190254 A1 | 7/2010 | Chian et al. |
| 2010/0233115 A1 | 9/2010 | Patel et al. |
| 2010/0273258 A1 | 10/2010 | Lannutti et al. |
| 2010/0291182 A1 | 11/2010 | Palasis et al. |
| 2010/0292791 A1 | 11/2010 | Lu et al. |
| 2010/0297208 A1 | 11/2010 | Fry et al. |
| 2010/0330419 A1 | 12/2010 | Cui et al. |
| 2010/0331980 A1 | 12/2010 | Lee et al. |
| 2011/0087277 A1 | 4/2011 | Viola et al. |
| 2011/0098826 A1 | 4/2011 | Mauck et al. |
| 2011/0101571 A1 | 5/2011 | Reneker |
| 2011/0111012 A1 | 5/2011 | Pepper et al. |
| 2011/0150973 A1 | 6/2011 | Bowlin et al. |
| 2011/0152897 A1 | 6/2011 | Bates |
| 2011/0174158 A1 | 7/2011 | Walls et al. |
| 2011/0180951 A1 | 7/2011 | Teo et al. |
| 2011/0242310 A1 | 10/2011 | Beebe, Jr. et al. |
| 2011/0280919 A1 | 11/2011 | Moloye-Olabisi et al. |
| 2011/0287082 A1 | 11/2011 | Smith et al. |
| 2012/0015331 A1 | 1/2012 | Wood et al. |
| 2012/0029654 A1 | 2/2012 | Xu et al. |
| 2012/0040581 A1 | 2/2012 | Kim |
| 2012/0123342 A1 | 5/2012 | Andrews et al. |
| 2012/0165957 A1* | 6/2012 | Everland ............ A61L 27/58 623/23.72 |
| 2012/0225039 A1 | 9/2012 | Li et al. |
| 2012/0265300 A1 | 10/2012 | Mauck et al. |
| 2012/0310260 A1 | 12/2012 | Hamlin et al. |
| 2012/0330437 A1 | 12/2012 | El-Kurdi et al. |
| 2013/0035704 A1 | 2/2013 | Dudai |
| 2013/0110138 A1 | 2/2013 | Hurtado et al. |
| 2013/0115457 A1 | 5/2013 | Haynie et al. |
| 2013/0197663 A1 | 8/2013 | MacEwan et al. |
| 2013/0251762 A1 | 9/2013 | Wei et al. |
| 2013/0338791 A1 | 12/2013 | McCullen et al. |
| 2014/0030315 A1* | 1/2014 | Johnson ............ A61K 9/70 424/444 |
| 2014/0081297 A1 | 3/2014 | Hoke et al. |
| 2014/0128345 A1 | 5/2014 | Woodrow et al. |
| 2014/0272225 A1 | 9/2014 | Johnson |
| 2014/0303727 A1 | 10/2014 | Atlas et al. |
| 2014/0322512 A1 | 10/2014 | Pham et al. |
| 2015/0045818 A1 | 2/2015 | Kim et al. |
| 2015/0132423 A1 | 5/2015 | Johnson |
| 2015/0190285 A1 | 7/2015 | MacEwan |
| 2015/0250927 A1 | 9/2015 | MacEwan |
| 2015/0297791 A1 | 10/2015 | Patel et al. |
| 2015/0342719 A1 | 12/2015 | Chen et al. |
| 2016/0022873 A1 | 1/2016 | Besner et al. |
| 2016/0083692 A1 | 3/2016 | Hardy et al. |
| 2016/0083868 A1 | 3/2016 | Park |
| 2016/0136330 A1 | 5/2016 | Benkirane-Jessel et al. |
| 2016/0302869 A1 | 10/2016 | Chopra |
| 2016/0317706 A1* | 11/2016 | Johnson ............ D04H 1/728 |
| 2017/0095591 A1 | 4/2017 | Zuhaib et al. |
| 2017/0119886 A1 | 5/2017 | Johnson et al. |
| 2017/0182206 A1 | 6/2017 | Johnson et al. |
| 2017/0182211 A1 | 6/2017 | Raxworthy et al. |
| 2017/0319323 A1 | 11/2017 | MacEwan |
| 2017/0319742 A1 | 11/2017 | Johnson et al. |
| 2017/0326270 A1 | 11/2017 | MacEwan |
| 2018/0116973 A1 | 5/2018 | Johnson |
| 2018/0161185 A1 | 6/2018 | Kresslein et al. |
| 2018/0174367 A1 | 6/2018 | Marom et al. |
| 2018/0221537 A1 | 8/2018 | Johnson et al. |
| 2018/0237952 A1 | 8/2018 | Johnson et al. |
| 2018/0245243 A1 | 8/2018 | Krieger et al. |
| 2018/0263919 A1 | 9/2018 | Hoke et al. |
| 2018/0368917 A1 | 12/2018 | Dekel et al. |
| 2019/0015563 A1 | 1/2019 | MacEwan |
| 2019/0021837 A1 | 1/2019 | MacEwan et al. |
| 2019/0054036 A1 | 2/2019 | Johnson et al. |
| 2019/0102880 A1 | 4/2019 | Parpara et al. |
| 2019/0105128 A1 | 4/2019 | Velazquez et al. |
| 2019/0134267 A1 | 5/2019 | Francis et al. |
| 2019/0134570 A1 | 5/2019 | Pintauro et al. |
| 2019/0153398 A1 | 5/2019 | Johnson |
| 2019/0249127 A1 | 5/2019 | Johnson |
| 2019/0175786 A1 | 6/2019 | Cohen et al. |
| 2019/0269829 A1 | 9/2019 | Johnson et al. |
| 2019/0271098 A1 | 9/2019 | Johnson et al. |
| 2019/0328393 A1 | 10/2019 | Yu et al. |
| 2019/0330419 A1 | 10/2019 | Song et al. |
| 2019/0350688 A1 | 11/2019 | Hurtado et al. |
| 2019/0365520 A1 | 12/2019 | MacEwan |
| 2019/0365958 A1 | 12/2019 | MacEwan |
| 2019/0374227 A1 | 12/2019 | Johnson et al. |
| 2020/0000570 A1 | 1/2020 | MacEwan et al. |
| 2020/0060800 A1 | 2/2020 | MacEwan et al. |
| 2020/0197153 A1 | 6/2020 | MacEwan et al. |
| 2020/0229679 A1 | 7/2020 | Zhao et al. |
| 2020/0242767 A1 | 7/2020 | Zhao et al. |
| 2020/0277711 A1 | 9/2020 | Xie |
| 2020/0390932 A1 | 12/2020 | MacEwan |
| 2021/0001014 A1 | 1/2021 | MacEwan |
| 2021/0030525 A1 | 2/2021 | MacEwan et al. |
| 2021/0052362 A1 | 2/2021 | MacEwan et al. |
| 2021/0228782 A1 | 7/2021 | MacEwan |
| 2021/0267746 A1 | 9/2021 | MacEwan et al. |
| 2021/0338408 A1 | 11/2021 | MacEwan et al. |

FOREIGN PATENT DOCUMENTS

| | | |
|---|---|---|
| CA | 2094908 C | 2/2000 |
| CA | 2386810 C | 9/2013 |
| CA | 2802482 | 6/2017 |
| CN | 102260963 | 11/2011 |
| CN | 102691176 | 9/2012 |
| CN | 103599562 | 2/2014 |
| CN | 104894750 | 9/2015 |
| DE | 102014107826 A1 | 12/2014 |
| EP | 0515522 B1 | 10/1993 |
| EP | 0571415 | 7/1995 |
| EP | 0757127 | 2/1997 |
| EP | 2045375 | 3/2011 |
| EP | 2358301 | 8/2011 |
| EP | 2599858 | 6/2013 |
| EP | 2582868 | 3/2018 |
| EP | 2897561 | 4/2020 |
| EP | 3508641 | 8/2020 |
| EP | 3741896 | 11/2020 |
| GB | 1286858 | 8/1972 |
| GB | 2181207 | 4/1987 |
| GB | 2195251 | 4/1988 |
| JP | H03161563 | 7/1991 |
| JP | 3487722 B2 | 1/2004 |
| JP | 2005-534828 | 11/2005 |
| JP | 2006-283241 | 10/2006 |
| JP | 2006-328562 | 12/2006 |
| JP | 2007-303021 | 11/2007 |
| JP | 2008-223186 | 9/2008 |
| JP | 2009061109 | 3/2009 |
| JP | 2011-509786 | 3/2011 |
| JP | 4769871 | 9/2011 |
| JP | 4979264 | 7/2012 |
| JP | 2012-528464 | 11/2012 |
| JP | 2013-518996 | 5/2013 |
| JP | 2013-534979 | 9/2013 |
| JP | 6295258 | 3/2018 |
| JP | 6328672 | 5/2018 |
| KR | 100439871 B1 | 7/2004 |
| KR | 20060118937 | 11/2006 |
| KR | 10-2007-0047873 | 5/2007 |
| KR | 10-1703095 | 2/2017 |
| SG | 186379 | 1/2013 |
| SG | 11201502207 W | 4/2015 |
| WO | WO 1991/001695 | 2/1991 |
| WO | WO 01/27365 | 4/2001 |
| WO | WO 02/00149 | 1/2002 |
| WO | WO 2004/016839 | 2/2004 |
| WO | WO 2006/096791 | 9/2006 |

(56) References Cited

FOREIGN PATENT DOCUMENTS

| | | |
|---|---|---|
| WO | WO 2006/123858 | 11/2006 |
| WO | WO 2007/086910 | 8/2007 |
| WO | WO 2008/069760 | 6/2008 |
| WO | WO 2009/093023 | 7/2009 |
| WO | WO 2010/041944 | 4/2010 |
| WO | WO 2010/042651 | 4/2010 |
| WO | WO 2010/112564 | 10/2010 |
| WO | WO 2010138619 | 12/2010 |
| WO | WO 2011/095141 | 8/2011 |
| WO | WO 2011/159889 | 12/2011 |
| WO | WO 2012/080706 | 6/2012 |
| WO | WO 2013/106822 | 1/2013 |
| WO | WO 2013/025819 | 2/2013 |
| WO | WO 2013/050428 | 4/2013 |
| WO | WO 2013/078051 | 5/2013 |
| WO | WO 2014/031721 | 2/2014 |
| WO | WO 2014046669 | 3/2014 |
| WO | WO 2014/145864 | 9/2014 |
| WO | WO 2014/152906 | 9/2014 |
| WO | WO 2015/048224 | 4/2015 |
| WO | WO 2015/116917 | 8/2015 |
| WO | WO 2015/153011 | 10/2015 |
| WO | WO 2015/157485 | 10/2015 |
| WO | WO 2016/176559 | 11/2016 |
| WO | WO 2017/024263 | 2/2017 |
| WO | WO 2017/035500 | 3/2017 |
| WO | WO 2017/044982 | 3/2017 |
| WO | WO 2017/079328 | 5/2017 |
| WO | WO 2017/196325 | 11/2017 |
| WO | WO 2018/112203 | 6/2018 |
| WO | WO 2018/144858 | 8/2018 |

OTHER PUBLICATIONS

ASTM International, "Standard Guide for Assessing Microstructure of Polymeric Scaffolds for Use in Tissue-Engineered Medical Products" dated Mar. 27, 2013.
Australian Examination Report issued for Application No. 2011268321, dated Apr. 17, 2015 (4 pages).
Australian Examination Report No. 1 issued for Application No. 2012390291 dated May 31, 2017 (4 pages).
Australian Examination Report No. 1 issued for Application No. 2017232208 dated Jan. 8, 2018 (4 pages).
Australian Examination Report No. 1 issued for Application No. 2016406314 dated Oct. 29, 2020 (4 pages).
Australian Examination Report No. 2 issued for Application No. 2016406314 dated Mar. 12, 2021.
Barbol T et al. Biocompalibility evaluation of dura maTer substitutes in an animal model. Neurological research 2001; vol. 23 pp. 813-820.
Beachley V et al. "Polymer nanofibrous structures: Fabrication, biofunctionalization, and cell interactions." Prog Polym Sci. 2010;35(7) pp. 868-892.
Beheshtkhoo et al. "Fabrication and Properties of Collagen and Polyurethane Polymeric Nanofibers Using Electrospinning Techniques" Journal of Environmental Treatment Techniques 2019, vol. 7, Issue 4, pp. 802-807.
Bhattarai et al. "Electrospun chitosa-based nanofibers and their cellular compatibility", Biomaterials vol. 26, Issue 31, Nov. 2005, pp. 6176-6184.
Bognitzki et al., "Preparation of Fibers with Nanoscaled Morphologies: Electrospinning of Polmer Blends" Polymer Enginering and Science, Jun. 2001, vol. 41, No. 6, pp. 982-989.
Bognitzki et al., "Nanostructured Fibers via Electrospinning**", Advanced Mater. 2001, 13. No. 1, Jan. 5, pp. 70-72.
Brazil Technical Report for related Application No. BR112012032169-2, dated Feb. 20, 2019, 4 pages.
Brazil Technical Report for related Application No. BR112015006301-2, dated Oct. 15, 2020, 5 pages.
Camposeo et al., "Lobal Mechanical Properties of Electrospun Fibers Correlate to Their Internal Nanostructure" Nano Lett. 2013, pp. 13, 5056-5062.

Canadian Examiner's Report issued for Application No. 2,885,682, dated Jun. 4, 2018 (5 pages).
Chen, Rui, et al. "Preparation and characterization of coaxial electrospun thermoplastic polyurethane/collagen compound nanofibers fortissue engineering applications." Colloids and Surfaces B: Biointerfaces 79.2 (2010) pp. 315-325.
Chen, Rui, et al. "Preparation and Study of TPU/Collagen Complex Nanofiber via Electrospinning." AATCC review 10.2 (2010).
China Examiner's Report issued for Application No. 201680087078. 9, dated Jan. 20, 2021 with translation in 28 pages.
Choi, Sung-Seen, et al. "Formation of interfiber bonding in electrospun poly (etherimide) nanofiber web." Journal of materials science 39.4 (2004) pp. 1511-1513.
Cole et al. A comparative long-term assessment of four soft tissue substitutes. Aesthetic surgery journal I the American Society for Aesthetic Plastic surgery 2011; vol. 31 pp. 674-681.
Cui et al., "Controlled assembly of poly(vinyl pyrrolidone) fibers through an electric-field-assisted electrospinning method," Applied Physics A, 103(1): 167-172 (2011).
Davis, et al., "A biodegradable compsite artifical tendon," Journal of Materials Science: Materials in Medicine 3,359-364 (1992).
Deitzel et al. "The effect of processing variables on the morphology of electrospun nanofibers and textiles" Polymer 42 (2001) pp. 261-272.
Doshi, et al., "Electrospinning Process and Applications of Electrospun Fibers" 35 J. Electrostatics 151 (1995).
Dzenis et al., "Hierarchical nano-/micromaterials based on electrospun polymer fibers: Predictive models for thermomechanical behavior" Journal of Computer-Aided Materials Design, pp. 3, 403-408 (1996).
Dzenis et al., "Polymer Hybrid Nano/Micro Composites," Proceedings of the American Society for Composites Ninth Technical Conference, pp. 657-665, 1994.
European Examination Report issued for Application No. 12884789.4 dated Feb. 13, 2018 (5 pages).
European Extended Search Report issued for Application No. 11796426.2, dated Mar. 27, 2014 (6 pages).
European Extended Search Report issued for Application No. 12884789, dated Jun. 16, 2016 (12 pages).
European Supplementary Partial Search Report issued for Application No. 12884789, dated Feb. 29, 2016 (8 pages).
European Extended Search Report in Application No. 16901840.5 dated Dec. 2, 2019 in 10 pages.
European Search Report and Written Opinion for EP application No. 18164340, dated May 17, 2019, 5 pages.
Figallo et al. "Micropatterned biopolymer 3D scaffold for static and dynamic culture of human fibroblasts" Biotechnol Prog . Jan.-Feb. 2007;23(1):210-6. doi: 10.1021/bp0602092.
Foy, et al., Allergic reaction to a bovine dural substitute following spinal cord untethering. Case report, Journal of Neurosurgery Pediatrics 2008; vol. 1, pp. 167-169.
GCC Examination Report in Application No. GC 2017-33397 dated Apr. 15, 2019 in 4 pages.
Gibson, et al., Electrospun Fiber Mais: Transport Properties, AlChE Journal, 1999, vol. 45, No. 1, pp. 190-195.
Huang, et al., "Generation of Synthetic Elastin-Mimetic Small Diameter Fibers and Fiber Networks", Macromolecules 2000, 33, 2989-2997.
Indian Examination Report issued for Application No. 11141/DELNP/2012, dated Jun. 21, 2018 (7 pages).
Indian First Examination Report for IN Application No. 2299/DELNP/2015, dated Oct. 24, 2019, 6 pages.
Jaeger, et al. "Electrospinning of Ultra-Thin Polymer Fibers", Macromol. Symp. 127, 141-150 (1998).
Japanese Office action issued for Application No. 2013-515511, dated Oct. 28, 2014.
Japanese Office Action Summary issued for Application No. 2015-533026, dated Oct. 18, 2016 (5 pages).
Japanese Office translation issued for Application No. 2015-533026, dated Jun. 27, 2017 (4 pages).
Li et al., "Direct Fabrication of Composite and Ceramic Hollow Nanofibers by Electrospinning" Nano Lett. 2004, 4, 933-938.
Li, et al., "Electrospinning Nanofibers as Uniaxially Aligned Arrays and Layer-by-Layer Stacked Films" Adv. Mater. 2004, 16, 361-36.

(56) References Cited

OTHER PUBLICATIONS

Li et al., "Electrospinning of Nanofibers: Reinventing the Wheel?" Adv. Mater. 11.2004, 16, 1151-1170.

Li, et al., "Electrospinning of Polymeric and Ceramic Nanofibers as 20 Uniaxially Aligned Arrays" Nano Lett. 2003, 3, 1167-1171.

Liu, L-Q et al. "Tensile mechanics of electrospun multiwalled nanotube/poly (methyl methacrylate) nanofibers." Advanced Materials 19.9 (2007) pp. 1228-1233.

Martinez-Lage et al., "Accidental transmission of Creutzfeldt-Jakob disease by dural cadaveric grafts," Journal of Neurology, Neurosurgery & Psychiatry, 57(9): 1091-1094 (1994).

Mcmillan et al. "Small diameter porous poly (s-caprolactone) films enhance adhesion and growth of human cultured epidermal keratinocyte and dermal fibroblast cells", Tissue Eng. (2007) Apr. 13(4): pp. 789-798.

Mi et al. "Asymmetric chitosan membranes prepared by dry/west phase separation: a new type of wound dressing for controlled antibacterial release", Journal of Membrane Science, (vol. 212) pp. 237-254.

Norris et al. "Electrostatic fabrication of ultrafine conducting fibers: polyaniline/polyethylene oxide blends" Synthetic Metals 114 (2000) pp. 109-114.

Park, S. et al., Apparatus for Preparing Electrospun Nanofibers: Designing and Electrospinning process for Nanofiber Fabrication, Polymer International, 2007, pp. 1361-1366.

PCT International Search Report and Written Opinion of International Application No. PCT/US2012/056548 dated Apr. 26, 2013 in 14 pages.

PCT International Search Report and Written Opinion issued for Application No. PCT/2011/040691, dated Feb. 24, 2012.

PCT International Preliminary Report on Patentability for PCT/US2011/040691, dated Dec. 19, 2012, 9 pages.

PCT International Search Report in International Application No. PCT/US16/32001 dated Aug. 11, 2016 in 1 page.

Pham et al. "Electrospun poly (ε-caprolactone) microfiber and multilayer nanofiber/microfiber scaffold: characterization of scaffolds and measurement of cellular infiltration", Biomacromolecules 2006, pp. 7, 10, 2796-2805, Pub. Sep. 23, 2006.

Shin, Ho Joon, et al. "Electrospun PLGA nanofiber scaffolds for articular cartilage reconstruction: mechanical stability, degradation and cellular responses under mechanical simulation in vitro." Journal of Biomaterials Science, Polymer Edition 17.1-2 (2006) pp. 103-119.

Singapore Examination Report issued for Application No. 11201502207W, dated Jun. 13, 2017 (8 pages).

Singapore Search and Examination Report for SG 2012092888, dated May 15, 2014, 17 pgs.

Singapore Search and Examination Report for SG 2012092888, dated Jan. 30, 2015, 8 pgs.

Tan et al., "Tensile test of a single nanofiber using an atomic force microscope tip", Applied Physics Letters 86, 073115 (2005).

Teo W et al. "Electrospun scaffold tailored for tussie-specific extracellular matrix." Biotechnol J Healthc Nutr Technol. 2006;1(9):918-29.

Thomas et al. "Electrospun bioactive nanocomposite scaffolds of polycaprolactone and nanohydroxyapatite for bone tissue engineering", J Nanosci Nanotechnol. Feb. 2006;6(2):487-93. doi: 10.1166/jnn.2006.097.

Tormala, et al., "Ultra-High-Strength absorable self-reinforeced polyglycolide (SR-PGA) composite rods for internal fixation of bone fractures: In vitro and in vivo study" Journal of Biomedical Materials Research, Jan. 1991.

Vaz et al. "Design of scaffold for blood vessel tissue engineering using a multiple-layering electrospinning technique" Acta Biomater/Sep. 2005;1(5):572-82. doi:10.1016/j.actbio.2005.06.006. Epub Jul. 26, 2005. https://pubmed.ncbi.nlm.nih.gov/16701837/.

Wikipedia, "Polyhydroxyethylmethacrylate," downloaded on Dec. 18, 2019 from.

WISE Histologic proof that acellular dermal matrices (ADM)—Enduragen DermaMalrixand DuraMatrix-are not repopulaled or nonviable and that AlloDerm may be repopulated but degraded synchronously. Aesthetic surgery Journal / the American Society for Aesthetic Plastic surgery 2012; vol. 32 pp. 355-358.

Xie, et al., Conductive core-sheath nanofibers and their potential applications in neural tissue engineering. Adv Funct Mater 2009; 19, 2312-2318.

Xie, et al., Neurites outgrowth on nanofiber scaffolds with different orders, structures, and surface properties. ACS Nano 2009; 3, 1151-1159.

Xie et al., Putting electrospun nanofibers to work for biomedical research. Macromol Rapid Commun 2008; 29, 1775-1792.

Xie, et al., Radially Aligned, Electrospun Nanofibers as Dural Substitutes for Wound Closure and Tissue Regeneration Applicalion, ACS Nano, 2010, vol. 4, No. 9, pp. 5027-5036.

Zerris, et al., Repair of the dura mater with processed collagen devices. Journal of biomedical materials research Part B, Applied biomaterials 2007; vol. 83, pp. 580-588.

Zong, Xinhua, et al. "Structure and process relationship of electrospun bioabsorbable nanofiber membranes." Polymer 43.16 (2002) pp. 4403-4412.

U.S. Appl. No. 62/154,286, filed Apr. 29, 2015, Johnson.

Cheng et al, "Engineering the Microstructure of Electrospun Fibrous Scaffolds by Microtopography," Biomacromolecules 14:1349-1360 (2013), doi: 10.1021/bm302000n).

Declaration of Gary E. Wnek, PH.D. in support of Petition for Inter Partes Review of U.S. Pat. No. 10,632,228.

Dubsky et al., "Nanofibers prepared by needleless electrospinning technology as scaffolds for wound healing," J Mater Sci: Mater Med, DOI 10.1007/s 10856-012-4577-7, Feb. 2012.

European Search Report and Written Opinion for EP application No. 20175280.5, dated Sep. 11, 2020 in 8 pages.

Fang et al. "Electrospinning: an advanced nanofiber production technology." In: H. Niu, H. Zhou and H. Wang (Eds.), Energy Harvesting Properties of Electrospun Nanofibers (1st ed. [online], pp. 1-1-1-44). IOP Publishing Ltd. (2020). https://iopscience.iop.org/book/978-0-7503-2005-4/chapter/bk978-0-7503-2005-4ch1 (Accessed Apr. 6, 2021), doi 10.1088/978-0-7503-2005-4ch1.

Khil et al., "Novel Fabricated Matrix Via Electrospinning for Tissue Engineering," Wiley Periodicals, Inc. 2004.

Kumar et al., "Nanofibers: Effective Generation by Electrospinning and Their Applications," Journal of Nanoscience and Nanotechnology, vol. 12, 1-25, 2012.

Liu et al, "Electrospun Fibrous Mats on Lithographically Micropatterned Collectors to Control Cellular Behaviors," Langmuir 28:17134-17142 (2012), doi: 10.1021/la303490x).

Madhugiri, S. et al., "Electrospun MEH-PPV/SBA-15 Composite Nanofibers Using a Dual Syringe Method," J. Am. Chem. Soc., 125: 14531-14538 (2003).

Petition for Inter Partes Review of U.S. Pat. No. 10,632,228 dated May 28, 2021 in 91 pages.

Pham et al., "Electrospinning of Polymeric Nanofibers for Tissue Engineering Applications: A Review", Tissue Engineering, 12(5): 1197-1211 (2006).

Rieger et al. "Designing electrospun nanofiber mats to promote wound healing—a review," J. Mater. Chem. B, 2013, 1, 4531.

Subbiah et al. "Electrospinning of Nanofibers," J. of Applied Polymer Science, 96: 557-569 (2005).

Valizadeh et al., "Electrospinning and electrospun nanofibres," IET Nanobiotechnol., 2014, vol. 8, Iss. 2, pp. 83-92.

Yarin, et al., "Taylor Cone and Jetting from Liquid Driplets in Electrospinning of Nanofibers," (2001). College of Polymer Science and Polymer Engineering. 85.

Yogeshwar et al., "Electrospinning of Type I Collagen and PCL Nanofibers Using Acetic Acid," Wiley Online Library, Feb. 1, 2012.

Australian Examination Report No. 3 issued for Application No. 2016406314 dated Jul. 5, 2021.

Chen et al. "Electrospun 3D Fibrous Scaffolds for Chronic Wound Repair," 2016, Materials 9(272):1-12.

China Second Office Action for Application No. 201680087078.9 dated Jul. 14, 2021 with translation in 28 pages.

Clark et al. "Investigation of the Effects of Cell Seeding on Neotissue Formation in a Tissue Engineered Trachea" J Pediatr Surg. Jan. 2016; 51(1) 49-55.

(56) References Cited

OTHER PUBLICATIONS

Dhandayuthapani et al. "Polymeric Scaffolds in Tissue Engineering Application: A Review" 2011, International Journal of Polymer Science 2011, Article ID 290602, 19 pages.
Manavitehrani et al. "Biomedical Applications of Biodegradable Polyesters" 2016, Polymers 8(20):1-32.
Murthy et al. "Biodegradation of Polymers" 2012, Polymer Science: A Comprehensive Reference, 9:547-560.
Pepper et al., "Factors Influencing Poor Outcomes in Synthetic Tissue-Engineered Tracheal Replacement" Otolaryngol Head Neck Surg. Sep. 2019; 161(3): 458-467.
Schneider et al. "Influence of pH on Wound-healing: a New Perspective for Wound-therapy" 2007 Arch. Dermatol. Res. 298:413-420.
Boland et al., "Tissue Engineering Scaffolds," Encyclopedia of Biomaterials and Biomedical Engineering 1: 1630-1638 (2004), doi: 10.1081/E-EBBE-120005552.
Boland et al., "Tailoring Tissue Engineering Scafforlds Using Elactrostatic Proceedings Techniques: A Study of Poly(Glycolic acid) Electrospinning," Journal of Macromolecular Science 38:1231-1243 (2001), doi: 10.1081/MA-100108380.
Chong et al., "Evaluation of electrospun PCL/gelatin nanofibrous scaffold for wound healing and layered dermal reconstruction," Acta Biomaterialia 3:321-330 (2007) doi: 10.1016/j.actbio.2007.10.002 (2007).
Defendants' Initial Invalidity Contentions in Civil Action No. 20-980-CFC-JLH dated Nov. 4, 2021 in 618 pages.
Dempsey et al., "Micropatterning of Electrospun Polyurethane Fibers Through Control of Surface Topography," Macromolecular Materials and Engineering 295: 990-994 (2020), doi: 10.1002/mame.201000152.
Diaz et al., "Fabrication of structured micro and nanofibers by coaxial electrospinning," Journal of Physics, Conference Series 127: 1-8 (2008), goi: 10.1088/1742-6596/127/1/012008.
Ding et al., "Fabrication of blend biodegradeable nanofibrous nonwoven mats via multi-jet electrospinning," Polymer 45: 1895-1902 (2004), doi: 10.1016/j.polymer.2004.01.026.
Fridrikh, et al., "Controlling the Fiber Diameter during Electrospinning" The American Physical Society 2003; vol. 90, No. 14.
Grafe et al., "Nanofiber Webs from Electrospinning," Nonwovens in Filtration—Fifth International Conference (2003).
Huang et al., "A review on polymer nanofibers by electrospinning and their applications in nanocomposites," Composites Science and Technology 63: 2223-2253 (2003), doi: 10.1016/S0266-3538(03)00178-7.

Ju et al., "Bilayered scaffold for engineering cellularized blood vessels," Biomaterials 31: 4313-4321 (2010), doi: 10.1016/j.biomaterials.2010.02.002.
Kenawy et al., "Release of tetracycline hydrochloride from electrospun poly(ethylene-co-vinylacetate), poly(lactic acid), and a blend," Journal of Controlled Release 81: 57-64 (2002), doi: 10.1016/S0168-3659(02)00041-X.
Kidoaki et al., "Mesoscopic spatial designs of nano- and microfiber meshes for tissue-engineering matrix and scaffold based on newly devised multilayering and mixing electrospinning techniques," Biomaterials 26: 37-46 (2005), doi: 10.1016/j.biomaterials.2004.01.063.
Le et al., "Engineering a Biocompatible Scaffold with Either Micrometre or Nanometre Scale Surface Topography for Promoting Protein Adsorption and Cellular Response," International Journal of Biomaterials 2013: 1-16 (2013), doi: 10.115/2013/782549.
Lee et al., "Development of a composite vascular scaffolding system that withstands physiological vascular conditions," Biomaterials 29: 2891-2898 (2008), doi: 10.1016/j.biomaterials.2008.03.032.
McClure et al., "The use of air-flow impedance to control fiber deposition patterns during electrospinning," Biomaterials 33: 771-779 (2012), doi: 10.1016/j.biomaterials.2011.10.011.
Ramakrishna et al., "Electrospun nanofibers: solving global issues," Materials Today 9: 40-50 (2006), doi: 10.1016/S1369-7021 (06)71389-X.
Smith et al., "Suture-reinforced electrospun polydioxanone-elastin small-diameter tubes for use in vascular tissue engineering: a feasibility study," Acta Biomaterialia 4: 58-66 (2008), doi: 10.1016/j.actbio.2007.08.001.
Stitzel et al., "Arterial Smooth Muscle Cell Proliferation on a Novel Biomimicking, Biodegradeable Vascular Graft Scaffold," Journal of Biomaterials Applications 16: 22-33 (2001), doi: 10.1106/U2UU-M9QH-Y0BB-5GYL.
Wulkersdorfer, "Bimodal Porous Scaffolds by Sequential Electrospinning of Poly(glycolic acid) with Sucrose Particles," International Journal of Polymer Science 2010: 1-9 (2010), doi: 10.1155/2010/436178.
European Office Action for application No. 16901840.5, dated Sep. 10, 2021.
Indian Frist Examination Report for IN Application No. 201817046790, dated Sep. 29, 2021, 6 pages.
Shin, et al. "Experimental characterization of electrospinning: the electrically forced jet and instabilities" Polymer 42 (2001) 9955-9967.

\* cited by examiner

TISSUE SUBSTITUTE MATERIALS AND METHODS FOR TISSUE REPAIR

CROSS REFERENCE TO RELATED APPLICATIONS

The present application is a continuation U.S. patent application Ser. No. 16/816,084, filed Mar. 11, 2020 which is a continuation of U.S. patent application Ser. No. 15/152,726, filed May 12, 2016, now U.S. Pat. No. 10,632,228. Any and all applications for which a priority claim is identified here or in the Application Data Sheet as filed with the present application are hereby incorporated by reference under 37 CFR 1.57.

BACKGROUND OF THE DISCLOSURE

The present disclosure relates generally to non-woven graft materials for use in specialized surgical procedures such as neurosurgical procedures, wound repair, oral surgery, dermal repair and regeneration, head and neck surgery, endonasal surgery and bone repair, methods for making the non-woven graft materials, and methods for repairing tissue such as neurological tissue using the non-woven graft materials. More particularly, the present disclosure relates to non-woven graft materials including at least two distinct fiber compositions composed of different polymeric materials, methods for making the non-woven graft materials and methods for repairing tissue in an individual in need thereof using the non-woven graft materials.

Neurosurgical procedures commonly result in the perforation or removal of the watertight fibrous membrane surrounding the brain known as the dura mater. In all of these cases, the tissue barrier surrounding the brain must be repaired in a watertight manner in order to prevent damage to cortical tissues and leakage of cerebrospinal fluid. Dura substitutes are therefore needed to repair dural defects, reestablish the barrier that encloses the cerebrospinal space, and prevent cerebrospinal fluid (CSP) leakage and infection.

Numerous materials are currently in use as dura substitutes, including autograft, allograft, xenograft, and non-biologic synthetic materials. An ideal dura substitute should adequately restore the continuity of the dura mater and prevent CSP leak while minimizing infection. The mechanical properties of the material should facilitate suturing and/or tacking, yet also mimic the compliance of natural dura to allow ease of draping over delicate cortical tissues. Furthermore, an ideal dura substitute will minimize local tissue inflammation and preferably encourage the infiltration of cells and vasculature to expedite the reconstruction of native dura without inducing undesired outcomes of fibrosis or cortical adhesions.

Autograft materials utilized in dura repair are commonly acquired from a patient's own pericranium or facia latae. These tissues are desirable due to their minimal inflammatory response and their similarity to native dura. However, the use of these grafts is limited by the poor availability and host-site morbidity of the autograft material. Alternatively, human tissue is commonly utilized in the form of allografts, which are obtained from cadaveric dura. This tissue can be collected, sterilized, and stored to provide greater availability of graft material to repair large dura defects. However, significant risk of disease transmission limits the use of allografts in contemporary neurosurgical settings.

Xenograft materials are also commonly utilized as dura substitute products. Xenogenic materials are derived from bovine or porcine sources and are available in the form of decellularized tissues of the pericardium, small intestinal submucosa, and dermis or in the form of processed materials synthesized from collagen-rich sources such as the bovine Achilles tendon. Like allografts, xenografts have an inherent risk of zoonotic disease transmission and the potential to incite allergic and inflammatory reactions. Many biologic grafts have the advantage of being fully remodeled, whereby the natural components of the graft (e.g. collagen) recruit cell infiltration and angiogenesis that participate in the restructuring of the graft material. However, the rate at which a biologic graft is remodeled and resorbed is not well controlled, such that graft degradation can occur prematurely. This mismatch between graft resorption and native tissue regeneration can result in thin, weak tissue in the dura defect. The mechanical properties of xenograft materials also vary greatly due to differences in material processing such as crosslinking and protein denaturation. Select products have limited mechanical strength as to only be suitable for use as only grafts without the option of suturing. Other xenograft materials, however, provide the tear resistance and tensile strength required for suturing.

Some bovine-derived collagen materials are crosslinked to provide the mechanical strength necessary for suture repair of a dural defect. This manipulation of the mechanical properties can result in undesirable effects in the handling of the material, leading to a dura substitute with decreased compliance. Furthermore, the crosslinking of the bovine-derived collagen material has been shown to interfere with the degradation expected of its biologic collagen composition, leading to prolonged presence at the implant site with poorly defined material resorption. For biologically derived dura substitutes, desirable mechanical properties for suturability and desirable resorption properties for tissue remodeling are often mutually exclusive.

Despite the range of existing dura substitute materials available in contemporary neurosurgical clinics, there remains a need for a dura substitute that offers improved handling characteristics, mechanical properties, and safety compared to biologically derived grafts. Non-biologic synthetic materials have been explored to overcome the limitations of biologic grafts, whereby material strength, resorption, and safety can be controlled with much greater precision. Despite these offerings, tissue response to synthetic grafts has yet to be fully explored. Synthetic grafts also fall short in their approximation of the mechanical properties of the dura mater, such that these materials often have poor handling that complicates their clinical use.

Based on the shortcomings of the current clinically available materials, there remains a need for an improved resorbable non-biologic dura substitute that provides better handling and ease of use and improves the local tissue response during reconstruction of the native dura.

BRIEF DESCRIPTION OF THE DISCLOSURE

The present disclosure relates generally to non-woven graft materials, methods for making the materials, and methods for repairing neurological tissue such as dura mater using the materials.

In one aspect, the present disclosure is directed to a resorbable non-woven graft material comprising: a first non-woven fiber composition comprising poly(lactic-co-glycolic acid) and a second non-woven fiber composition comprising polydioxanone.

In another aspect, the present disclosure is directed to a resorbable non-woven graft material comprising: a first non-woven fiber composition, wherein the first fiber composition comprises a polymer selected from the group consisting of polycaprolactone, polydioxanone, poly(glycolic acid), poly(L-lactic acid), poly(lactide-co-glycolide), poly(L-lactide), poly(D,L-lactide), poly(ethylene glycol), montmorillonite, poly(L-lactide-co-ε-caprolactone), poly(ε-caprolactone-co-ethyl ethylene phosphate), poly[bis(p-methylphenoxy) phosphazene], poly(3-hydroxybutyrate-co-3-hydroxyvalerate), poly(ester urethane) urea, poly(p-dioxanone), polyurethane, polyethylene terephthalate, poly(ethylene-co-vinylacetate), poly(ethylene oxide), poly(phosphazene), poly(ethylene-co-vinyl alcohol), polymer nanoclay nanocomposites, poly(ethylenimine), poly(ethyleneoxide), poly vinylpyrrolidone, polystyrene (PS) and combinations thereof; and a second non-woven fiber composition, wherein the second fiber composition comprises a polymer selected from the group consisting of polycaprolactone, polydioxanone, poly(glycolic acid), poly(L-lactic acid), poly(lactide-co-glycolide), poly(L-lactide), poly(D,L-lactide), poly(ethylene glycol), montmorillonite, poly(L-lactide-co-ε-caprolactone), poly(ε-caprolactone-co-ethyl ethylene phosphate), poly[bis(p-methylphenoxy) phosphazene], poly(3-hydroxybutyrate-co-3-hydroxyvalerate), poly(ester urethane) urea, poly(p-dioxanone), polyurethane, polyethylene terephthalate, poly(ethylene-co-vinylacetate), poly(ethylene oxide), poly(phosphazene), poly(ethylene-co-vinyl alcohol), polymer nanoclay nanocomposites, poly(ethylenimine), poly(ethyleneoxide), poly vinylpyrrolidone; polystyrene and combinations thereof; and wherein the first fiber composition and the second fiber composition comprise different polymers.

In another aspect, the present disclosure is directed to a method for preparing a non-woven graft material, the method comprising: contacting a first fiber composition, wherein the first fiber composition comprises a polymer selected from the group consisting of polycaprolactone, polydioxanone, poly(glycolic acid), poly(L-lactic acid), poly(lactide-co-glycolide), poly(L-lactide), poly(D,L-lactide), poly(ethylene glycol), montmorillonite, poly(L-lactide-co-ε-caprolactone), poly(ε-caprolactone-co-ethyl ethylene phosphate), poly[bis(p-methylphenoxy) phosphazene], poly(3-hydroxybutyrate-co-3-hydroxyvalerate), poly(ester urethane) urea, poly(p-dioxanone), polyurethane, polyethylene terephthalate, poly(ethylene-co-vinylacetate), poly(ethylene oxide), poly(phosphazene), poly(ethylene-co-vinyl alcohol), polymer nanoclay nanocomposites, poly(ethylenimine), poly(ethyleneoxide), poly vinylpyrrolidone, polystyrene (PS) and combinations thereof; and a second fiber composition, wherein the second fiber composition comprises a polymer selected from the group consisting of polycaprolactone, polydioxanone, poly(glycolic acid), poly(L-lactic acid), poly(lactide-co-glycolide), poly(L-lactide), poly(D,L-lactide), poly(ethylene glycol), montmorillonite, poly(L-lactide-co-ε-caprolactone), poly(ε-caprolactone-co-ethyl ethylene phosphate), poly[bis(p-methylphenoxy) phosphazene], poly(3-hydroxybutyrate-co-3-hydroxyvalerate), poly(ester urethane) urea, poly(p-dioxanone), polyurethane, polyethylene terephthalate, poly(ethylene-co-vinylacetate), poly(ethylene oxide), poly(phosphazene), poly(ethylene-co-vinyl alcohol), polymer nanoclay nanocomposites, poly(ethylenimine), poly(ethyleneoxide), poly vinylpyrrolidone, polystyrene (PS) and combinations thereof; to form a non-woven graft material.

In accordance with the present disclosure, methods have been discovered that surprisingly allow for the repair of dura mater. The present disclosure has a broad and significant impact, as it allows for materials the overcome the shortcomings of existing materials and facilitates effective and reliable repair of native dura.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

DETAILED DESCRIPTION OF THE DISCLOSURE

Figure 1:
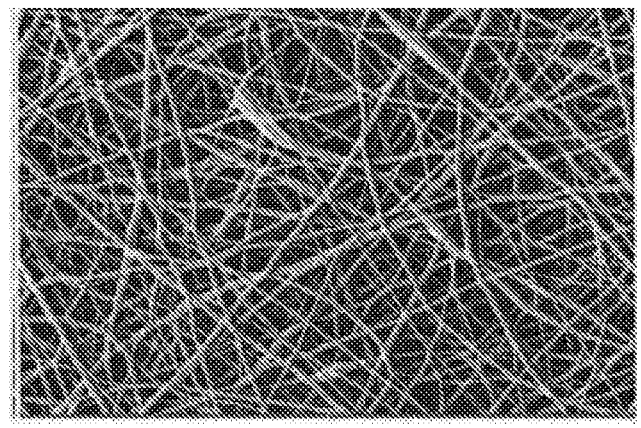
FIG. 1 is a scanning electron micrograph depicting an image of an exemplary non-woven fiber composition of the present disclosure.
Figures 2A, 2B:
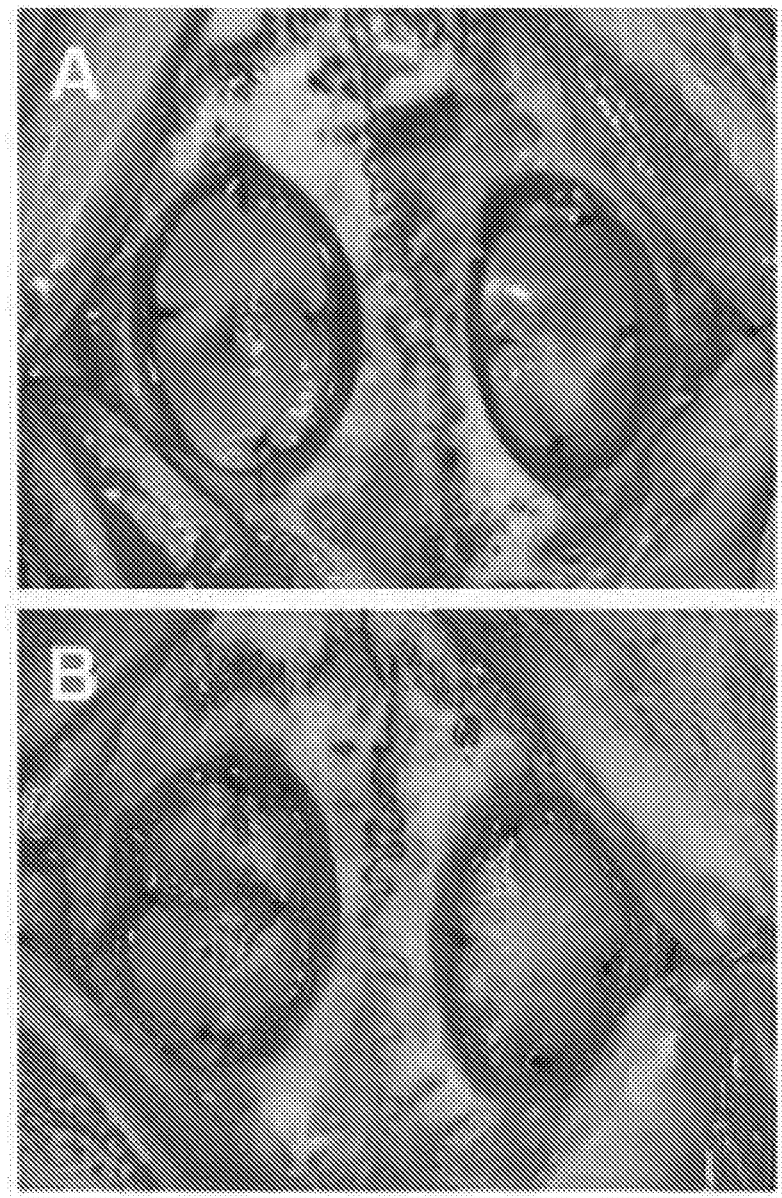
FIGS. 2A and 2B are photographic images depicting bilateral dural defects repaired with a non-woven graft material of the present disclosure (FIG. 2A) and a collagen graft material (FIG. 2B).

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the scope of the disclosure as defined by the appended claims.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Non-Woven Graft Materials of the Present Disclosure

Generally, the present disclosure is directed to non-woven graft materials including two or more distinct types of fiber compositions, each of which possesses independent mechanical, chemical and/or biological properties. For example, in one embodiment, inclusion of one fiber composition can stabilize the resulting non-woven graft material, while the other fiber composition can improve stability, free-shrinkage properties, mechanical properties, and resorption rate of the non-woven graft material.

As used interchangeably herein, "non-woven graft material" and "non-woven graft fabric" refer to a material having a structure of individual fibers or threads which are interlaid, but not in an identifiable manner as in a knitted fabric. Non-woven graft materials and non-woven graft fabrics can be formed from many processes such as for example, electrospinning processes, meltblowing processes, spunbonding processes, melt-spraying and bonded carded web processes. The basis weight of non-woven graft materials is usually expressed in ounces of material per square yard (osy) or grams per square meter (gsm) and the fiber diameters are usually expressed in nanometers and micrometers (microns). Suitable basis weight of non-woven graft materials of the present disclosure can range from about 50 gsm to about 300 gsm. More suitably, basis weight of non-woven graft materials of the present disclosure can range from about 70 gsm to about 140 gsm. The tensile strength of the non-woven graft material of the present disclosure can range from about 5 Newtons (N) to about 50 Newtons (N), including from about 1 N to about 10 N to about 15 N. The strength of the non-woven graft material of the present disclosure can also be described in terms of suture pull-out strength, which refers to the force at which a suture can be torn from the non-woven graft material. Suitable suture pull-out strength can range from about 1 N to about 5 N.

As used herein the term "microfibers" refers to small diameter fibers having an average diameter not greater than 75 microns, for example, having an average diameter of from about 0.5 microns to about 50 microns, or more particularly, microfibers having an average diameter of from about 2 microns to about 40 microns. Another frequently used expression of fiber diameter is denier. The diameter of a polypropylene fiber given in microns, for example, may be converted to denier by squaring, and multiplying the result by 0.00629, thus, a 15 micron polypropylene fiber has a denier of about 1.42 (15²×0.00629=1.415).

As used herein, the terms "nano-sized fibers" or "nanofibers" refer to very small diameter fibers having an average diameter not greater than 2000 nanometers, and suitably, not greater than 1500 nanometers (nm). Nanofibers are generally understood to have a fiber diameter range of about 10 to about 1500 nm, more specifically from about 10 to about 1000 nm, more specifically still from about 20 to about 500 nm, and most specifically from about 20 to about 400 nm. Other exemplary ranges include from about 50 to about 500 nm, from about 100 to 500 nm, or about 40 to about 200 nm.

As used herein the term "spunbonded fibers" refers to small diameter fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al.

As used herein the term "meltblown fibers" refers to fibers formed by extruding a molten thermoplastic material through a plurality of fine, usually circular, die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form randomly disbursed meltblown fibers. Such a process is disclosed, for example, in U.S. Pat. No. 3,849,241. Meltblown fibers are microfibers which may be continuous or discontinuous and are generally smaller than 10 microns in diameter.

As used herein, the term "electrospinning" refers to a technology which produces nano-sized fibers referred to as electrospun fibers from a solution using interactions between fluid dynamics and charged surfaces. In general, formation of the electrospun fiber involves providing a solution to an orifice in a body in electric communication with a voltage source, wherein electric forces assist in forming fine fibers that are deposited on a surface that may be grounded or otherwise at a lower voltage than the body. In electrospinning, a polymer solution or melt provided from one or more needles, slots or other orifices is charged to a high voltage relative to a collection grid. Electrical forces overcome surface tension and cause a fine jet of the polymer solution or melt to move towards the grounded or oppositely charged collection grid. The jet can splay into even finer fiber streams before reaching the target and is collected as interconnected small fibers. Specifically, as the solvent is evaporating (in processes using a solvent), this liquid jet is stretched to many times it original length to produce continuous, ultrathin fibers of the polymer. The dried or solidified fibers can have diameters of about 40 nm, or from about 10 to about 100 nm, although 100 to 500 nm fibers are commonly observed. Various forms of electrospun nanofibers include branched nanofibers, tubes, ribbons and split nanofibers, nanofiber yarns, surface-coated nanofibers (e.g., with carbon, metals, etc.), nanofibers produced in a vacuum, and so forth. The production of electrospun fibers is illustrated in many publication and patents, including, for example, P. W. Gibson et al., "Electrospun Fiber Mats: Transport Properties," AIChE Journal, 45(1): 190-195 (January 1999), which is hereby incorporated herein by reference.

As used herein, the term "type" such as when referring to "different types of fibers" or "distinct types of fibers" refers to fibers having "a substantially different overall material composition" with measurably different properties, outside of "average diameter" or other "size" differences. That is, two fibers can be of the same "type" as defined herein, yet have different "average diameters" or "average diameter ranges." Although fibers are of different "types" when they have a substantially different overall material composition, they can still have one or more components in common. For example, electrospun fibers made from a polymer blend with a first polymeric component present at a level of at least 10 wt % would be considered a different fiber type relative to electrospun fibers made from a polymer blend that was substantially free of the first polymeric component. Fibers of different "types" can also have a completely different content, each made of a different polymer for example, or one made from a polymer fiber and the other from a titania fiber, or a ceramic fiber and a titania fiber, and so on.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic and atactic symmetries.

The non-woven graft materials of the present disclosure typically include at least two distinct types of fiber compositions, each of which possesses independent mechanical, chemical and/or biological properties. The fiber compositions are suitably made of synthetic resorbable polymeric materials. As used herein, the term "resorbable polymeric material" refers to material formed from resorbable (also referred to as "bioabsorbable") polymers; that is the polymers possess the property to break down when the material is exposed to conditions that are typical of those present in a post-surgical site into degradation products that can be removed from the site within a period that roughly coincides with the period of post-surgical healing. Such degradation products can be absorbed into the body of the patient. The period of post-surgical healing is to be understood to be the period of time measured from the application of the non-woven graft material of the present disclosure to the time that the post-surgical site is substantially healed. This period can range from a period of several days to several months depending on the invasiveness of the surgical and the speed of healing of the particular individual. It is intended that the subject non-woven graft material can be prepared so that the time required for resorption of the non-woven graft material can be controlled to match the time necessary for healing or tissue reformation and regeneration. For example, in some non-woven graft materials of the present disclosure, the fiber compositions are selected to degrade within a period of about one week, while in other non-woven graft materials, the compositions are selected to degrade within a period of three years, or even longer if desired.

The fiber compositions used in the present disclosure can be produced from any resorbable material that meets the criteria of that material as those criteria are described above. The fiber compositions can be formed from resorbable polymers such as (but not limited to) polymers of lactic and glycolic acids, copolymers of lactic and glycolic acids, poly(ether-co-esters), poly(hydroxybutyrate), polycaprolactone, copolymers of lactic acid and ε-aminocaproic acid, lactide polymers, copolymers of poly(hydroxybutyrate) and 3-hydroxyvalerate, polyesters of succinic acid, poly(N-acetyl-D-glucosamine), polydioxanone, cross-linked hyaluronic acid, cross-linked collagen, and the like, and combinations thereof. Suitable synthetic polymers can be, for example, polycaprolactone (poly(ε-caprolactone), PCL), polydioxanone (PDO), poly(glycolic acid) (PGA), poly(L-lactic acid) (PLA), poly(lactide-co-glycolide) (PLGA), poly (L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(E-caprolactone-co-ethyl ethylene phosphate) (P(CL-EEP)), poly[bis(p-methylphenoxy) phosphazene] (PNmPh), poly (3-hydroxybutyrate-co-3-hydroxyvalerate) (PHBV), poly (ester urethane) urea (PEUU), poly(p-dioxanone) (PPDO), polyurethane (PU), polyethylene terephthalate (PET), poly (ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolidone; polystyrene (PS) and combinations thereof. Particularly suitable polymers include poly(lactic-co-glycolic acid), polydioxanone, polycaprolactone, and combinations thereof.

The fibers for the fiber compositions may be of a variety of sizes as deemed suitable by one skilled in the art for the end purpose of the non-woven graft material. Typically, the fibers have a mean fiber diameter of less than 5 μm, including less than 2 μm, including less than 1.5 μm, and including less than 1.0 μm. For example, in some embodiments, the fibers can have a mean fiber diameter ranging from about 10 nm to about 5 μm, more specifically from about 10 nm to about 1.0 μm, more specifically still from about 20 nm to about 500 nm, and most specifically from about 20 nm to about 400 nm. Other exemplary ranges include from about 50 nm to about 500 nm, from about 100 nm to about 500 nm, and about 40 nm to about 200 nm.

Suitable ratios of the first fiber composition to the second fiber composition resulting in the non-woven graft material can range from about 10 to 1 to about 1 to 10.

In one particularly suitable embodiment, the non-woven graft material is made from a first non-woven fiber composition prepared from poly(lactic-co-glycolic acid) and a second non-woven fiber composition prepared from polydioxanone. The resultant non-woven graft material is a non-biologic tissue substitute designed to provide optimal strength, handling, and suturability, while reducing local inflammation to provide improved wound healing and tissue regeneration. In an exemplary embodiment the non-woven graft material can be synthesized by electrospinning a first fiber composition including a copolymer of glycolide and L-lactide and a second fiber composition including polydioxanone (100 mol %) to create an architecture that is reminiscent of native extracellular matrix. The glycolide mol % to L-lactide mol % can range from about 100 mol % glycolide to 0 mol % L-lactide to 0 mol % glycolide to about 100 mol % L-lactide. A particularly suitable non-woven graft material includes a first fiber composition including a copolymer of glycolide and L-lactide having a glycolide mol % to L-lactide mol % ratio of 90 mol % glycolide and 10 mol % L-lactide. This method of synthesis creates a material that is mechanically strong, while providing the look and feel of native tissue. The architecture of this non-biologic graft material furthermore supports tissue ingrowth and neodurualization with minimal inflammation.

The non-woven graft material typically can be prepared to be any of a variety of sizes, shapes and thicknesses. Wet and dry non-woven graft material can suitably be cut and trimmed to any desired size and shape. In particularly suitable embodiments, the non-woven graft material has a size ranging from about 2.5 cm×2.5 cm (1 in×1 in) to about 25.5 cm×50 cm (10 in×20 in), including for example, from about 2.5 cm×2.5 cm (1 in×1 in), from about 5.0 cm×5.0 cm (2 in×2 in), from about 7.5 cm×7.5 cm (3 in×3 in), and including about 12.5 cm×17.5 cm (5 in×7 in).

The non-woven graft materials typically have a thickness ranging from about 0.1 mm to about 5 mm, including from about 0.3 mm to about 0.8 mm, about 0.3 mm to about 0.7 mm, and about 0.3 mm to about 0.5 mm.

The non-woven graft material is typically porous, and has interconnecting pores having a pore size in the range of from about 10 μm$^2$ to about 10,000 μm$^2$. Particularly suitable embodiments have a pore size of less than 300 μm$^2$. It is believed that pores of this size range can accommodate penetration by cells and can support the growth and proliferation of cells, followed by vascularization and tissue development.

In some aspects, the non-woven graft materials can be surface-modified with biomolecules such as (but not limited to) hyaluronans, collagen, laminin, fibronectin, growth factors, integrin peptides (Arg-Gly-Asp; i.e., RGD peptides), and the like, or by sodium hyaluronate and/or chitosan niacinamide ascorbate, which are believed to enhance cell migration and proliferation, or any combination thereof. The material can also be impregnated with these and other bioactive agents such as drugs, vitamins, growth factors, therapeutic peptides, and the like. In addition, drugs that would alleviate pain may also be incorporated into the material.

In another aspect, the present disclosure is directed to a laminate comprising a non-woven graft material, wherein the non-woven graft material includes a first non-woven fiber composition and a second non-woven fiber composition.

In one embodiment, the non-woven graft material of the laminate includes a first non-woven fiber composition including poly(lactic-co-glycolic acid) and a second non-woven fiber composition including polydioxanone, as described herein.

In another embodiment, the non-woven graft material can include at least one projection arising from a surface of the non-woven graft material. The projection is a protrusion or bulge arising from a surface of the non-woven graft material. The projection can arise from a top surface of the non-woven graft material, a bottom surface of the non-woven graft material, and a top surface and a bottom surface of the non-woven graft material. The projection can be any desired shape such as, for example, circular, spherical, square, rectangular, diamond, star, irregular, and combinations thereof. The projection can be any desired height as measured from the surface of the material to the top of the projection. In one embodiment, the projection can have a substantially uniform height from the surface of the material. In another embodiment, the projection can further form gradually from the surface of the material to the highest measurable surface of the projection. In some embodiments, a surface of the non-woven graft material includes a plurality of protrusions. The plurality of protrusions can be patterned or randomly distributed on a surface of the non-woven graft material. In another embodiment, the method includes forming at least one indentation in a surface of the non-woven graft material. The indentation is a recess or depression in a surface of the non-woven graft material. The indentation can in a top surface of the non-woven graft material, a bottom surface of the non-woven graft material, and a top surface and a bottom surface of the non-woven graft material. The indentation can be any desired shape such as, for example, circular, spherical, square, rectangular, diamond, star, irregular, and combinations thereof. The indentation can be any desired depth as measured from the surface of the material to the bottom of the indentation. In one embodiment, the indentation can have a substantially uniform depth from the surface of the material to the deepest depth of the indentation. In another embodiment, the indentation can further form gradually from the surface of the material to the deepest depth of the indentation. In some embodiments, a surface of the non-woven graft material includes a plurality of indentations. The plurality of indentations can be patterned or randomly distributed on a surface of the non-woven graft material. In another embodiment, the non-woven graft material can include at least one projection arising from a surface of the non-woven graft material and at least one indentation in the surface of the non-woven graft material. In another embodiment, the non-woven graft material can include at least one projection arising from a top surface of the non-woven graft material and at least one indentation in the top surface of the non-woven graft material. In another embodiment, the non-woven graft material can include at least one projection arising from a bottom surface of the non-woven graft material and at least one indentation in the bottom surface of the non-woven graft material. In another embodiment, the non-woven graft material can include at least one projection arising from a top surface of the non-woven graft material, at least one projection arising from a bottom surface of the non-woven graft material, at least one indentation in the top surface of the non-woven graft material, and at least one indentation in the bottom surface of the non-woven graft material. The plurality of indentations and the plurality of indentations can be patterned or randomly distributed on a surface of the non-woven graft material. Suitable methods for forming projections and indentations include pressing, stamping, and other methods known to those skilled in the art.

Methods of Making the Non-Woven Graft Materials

In another aspect, the present disclosure is directed to methods of preparing the non-woven graft materials. The methods generally include preparing aqueous solutions of the polymers described above. Particularly, fibers resulting from separate polymer solutions can be contacted together using one or more processes such as electrospinning, electrospraying, melt-blowing, spunbonding, to form the non-woven graft material; and drying the non-woven graft material.

The non-woven graft material is dried to remove solvents used to prepare the aqueous polymer solutions. Drying can be done using methods generally known in the art, including, without limitation, Yankee dryers and through-air dryers. Preferably, a non-compressive drying method that tends to preserve the bulk or thickness of the non-woven graft material is employed. Suitable through-drying apparatus and through-drying fabrics are conventional and well-known. One skilled in the art can readily determine the optimum drying gas temperature and residence time for a particular through-drying operation.

In one particular embodiment, a first fiber composition resulting from a first aqueous polymer solution and a second fiber composition resulting from a second aqueous polymer solution are blended to form a non-woven graft material using the electrospinning process as described above. The electrospinning process generally involves applying a high voltage (e.g., about 1 kV to about 100 kV, including about 3 kV to about 80 kV, depending on the configuration of the electrospinning apparatus) to a polymer fiber solution to produce a polymer jet. As the jet travels in air, the jet is elongated under repulsive electrostatic force to produce nanofibers from the polymer fiber solution. The high voltage is applied between the grounded surface (or oppositely charged surface) and a conducting capillary into which a polymer fiber solution is injected. The high voltage can also be applied to the solution or melt through a wire if the capillary is a nonconductor such as a glass pipette. Initially the solution at the open tip of the capillary is pulled into a conical shape (the so-called "Taylor cone") through the interplay of electrical force and surface tension. At a certain voltage range, a fine jet of polymer fiber solution forms at the tip of the Taylor cone and shoots toward the target. Forces from the electric field accelerate and stretch the jet. This stretching, together with evaporation of solvent molecules, causes the jet diameter to become smaller. As the jet diameter decreases, the charge density increases until electrostatic forces within the polymer overcome the cohesive forces holding the jet together (e.g., surface tension), causing the jet to split or "splay" into a multifilament of polymer nanofibers. The fibers continue to splay until they reach the collector, where they are collected as nonwoven nanofibers, and are optionally dried.

Suitable solvents for preparing aqueous polymer solutions include, for example, hexafluoroisopropanol (HFIP), dichloromethane (DCM), dimethylformamide (DMF), acetone, and ethanol.

In another embodiment, the method can further include forming at least one projection arising from a surface of the non-woven graft material, forming at least one indentation in a surface of the non-woven graft material, and combinations thereof. The projection is a protrusion or bulge arising from a surface of the non-woven graft material. The projection can arise from a top surface of the non-woven graft material, a bottom surface of the non-woven graft material, and a top surface and a bottom surface of the non-woven graft material. The projection can be any desired shape such as, for example, circular, spherical, square, rectangular, diamond, star, irregular, and combinations thereof. The projection can be any desired height as measured from the surface of the material to the top of the projection. In one embodiment, the projection can have a substantially uniform height from the surface of the material. In another embodiment, the projection can further form gradually from the surface of the material to the highest measurable surface of the projection. In some embodiments, a surface of the non-woven graft material includes a plurality of protrusions. The plurality of protrusions can be patterned or randomly distributed on a surface of the non-woven graft material. In another embodiment, the method includes forming at least one indentation in a surface of the non-woven graft material. The indentation is a recess or depression in a surface of the non-woven graft material. The indentation can in a top surface of the non-woven graft material, a bottom surface of the non-woven graft material, and a top surface and a bottom surface of the non-woven graft material. The indentation can be any desired shape such as, for example, circular, spherical, square, rectangular, diamond, star, irregular, and combinations thereof. The indentation can be any desired depth as measured from the surface of the material to the bottom of the indentation. In one embodiment, the indentation can have a substantially uniform depth from the surface of the material to the deepest depth of the indentation. In another embodiment, the indentation can further form gradually from the surface of the material to the deepest depth of the indentation. In some embodiments, a surface of the non-woven graft material includes a plurality of indentations. The plurality of indentations can be patterned or randomly distributed on a surface of the non-woven graft material. In another embodiment, the non-woven graft material can include at least one projection arising from a surface of the non-woven graft material and at least one indentation in the surface of the non-woven graft material. In another embodiment, the non-woven graft material can include at least one projection arising from a top surface of the non-woven graft material and at least one indentation in the top surface of the non-woven graft material. In another embodiment, the non-woven graft material can include at least one projection arising from a bottom surface of the non-woven graft material and at least one indentation in the bottom surface of the non-woven graft material. In another embodiment, the non-woven graft material can include at least one projection arising from a top surface of the non-woven graft material, at least one projection arising from a bottom surface of the non-woven graft material, at least one indentation in the top surface of the non-woven graft material, and at least one indentation in the bottom surface of the non-woven graft material. The plurality of indentations and the plurality of indentations can be patterned or randomly distributed on a surface of the non-woven graft material. Suitable methods for forming projections and indentations include pressing, stamping, and other methods known to those skilled in the art.

Methods of Tissue Repair

In another aspect, the present disclosure is directed to a method of tissue repair in an individual in need thereof. The method includes: applying a non-woven graft material to a surgical field, wherein the non-woven graft material comprises a first fiber composition and a second fiber composition. The method is particularly suitable for repairing tissues such as, for example, dura mater, pericardium, small intestinal submucosa, dermis, epidermis, tendon, trachea, heart valve leaflet, gastrointestinal tract, and cardiac tissue. Suitable tissue repair procedures include, for example, neurosurgeries such as dura mater repair, skin grafts, tracheal repair, gastrointestinal tract repair (e.g., abdominal hernia repair, ulcer repair), cardiac defect repair, head and neck surgeries, application to bone fractures, and burn repair.

Suitably, the non-woven graft material includes a first fiber composition, wherein the firs fiber composition includes a polymer selected from polycaprolactone (poly(ε-caprolactone), PCL), polydioxanone (PDO), poly(glycolic acid) (PGA), poly(L-lactic acid) (PLA), poly(lactide-co-glycolide) (PLGA), poly(L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy) phosphazene] (PNmPh), poly(3-hydroxybutyrate-co-3-hydroxyvalerate) (PHBV), poly(ester urethane) urea (PEUU), poly(p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolidone; polystyrene (PS) and combinations thereof. Particularly suitable polymers include poly(lactic-co-glycolic acid), polydioxanone, polycaprolactone, and combinations thereof.

Suitably, the non-woven graft material includes a second fiber composition, wherein the second fiber composition includes a polymer selected from polycaprolactone (poly(ε-caprolactone), PCL), polydioxanone (PDO), poly(glycolic acid) (PGA), poly(L-lactic acid) (PLA), poly(lactide-co-glycolide) (PLGA), poly(L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy) phosphazene] (PNmPh), poly(3-hydroxybutyrate-co-3-hydroxyvalerate) (PHBV), poly(ester urethane) urea (PEUU), poly(p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolidone; polystyrene (PS) and combinations thereof. Particularly suitable polymers include poly(lactic-co-glycolic acid), polydioxanone, polycaprolactone, and combinations thereof.

In a particularly suitable embodiment, the non-woven graft material includes a first fiber composition comprising poly(lactic-co-glycolic acid) and a second fiber composition comprising polydioxanone.

As used herein, "individual in need thereof" refers to an individual having a tissue defect, tissue damage, tissue that is missing due to damage or removal, and tissue damaged by incision. The methods are particularly suitable for use with an individual or subset of individuals having dura defects requiring repair of the dura mater. Individuals having dura defects can be those having a perforation in the dura mater, those having dura mater removed, those having damaged dura mater, and those having dura mater with a surgical incision.

The individual in need thereof can be an adult individual, a child, and a pediatric individual. Particularly suitable individuals can be a human. Other particularly suitable individuals can be animals such as primates, pigs, dogs, cats, rabbits, rodents (e.g., mice and rats), and the like.

In some embodiments, the non-woven graft material is secured to the surgical field, such as by suturing the non-woven graft material to the surgical field. In other embodiments, the non-woven graft material is secured to the surgical field, such as by a surgical adhesive.

EXAMPLES

Example 1

In this Example, the performance of a gold-standard xenogenic collagen graft material was compared to an exemplary embodiment of the non-woven graft material of the present disclosure.

Materials and Methods

Study Design

Ten female New Zealand White rabbits (5.0-5.5 months, Western Oregon Rabbit Company, Philomath, Oreg.) were randomized into two groups (I,II) of five animals each (n=5). Group I served as the positive control as all animals underwent bilateral craniotomy and dural resection followed by bilateral surgical repair of the induced dural defects utilizing a collagen graft material (Stryker, Inc. Kalamazoo, Mich.). Group II served as an experimental group as all animals underwent bilateral craniotomy and dural resection followed by bilateral surgical repair of the induced dural defects utilizing the fully resorbable non-biologic non-woven graft material. All animals underwent daily/weekly behavioral assessment and examination for signs of neurotoxicity, neurological sequelae, CSP leakage, and infection. Four weeks post-operatively all animals were euthanized and repair sites, including proximal skull and underlying cortical tissue, were explanted for histological and histopathological analysis. All animal procedures were performed in strict accordance with guidelines set by the Animal Welfare Act (AWA), the Association for Assessment and Accreditation of Laboratory Animal Care (AAALAC), and Institutional Animal Care and Use Committee (IACUC) of the University of Utah.

Surgical Procedure: Bilateral Craniotomy

Prior to surgery, all animals were administered butorphanol, acepromazine, cefazolin, and dexamethasone, as well as a transdermal fentanyl patch for prophylactic analgesia. All animals were anesthetized via ketamine and diazepam, administered intravenously via catheterization of the marginal ear vein, and maintained through the duration of the surgery via isoflurane. The cranium was then aseptically prepared and sterilized from the frontal ridge to the occiput. All hair was removed and the surgical site was prepared with povidone iodine and isopropyl alcohol. A 6-cm midline sagittal incision was then made extending through the scalp and the underlying periosteum. The periosteum was then elevated and retracted. Bilateral bone flaps were then created on either side of the skull utilizing a high-speed neurosurgical drill fitted with a matchstick bit. Resulting bone flaps measuring approximately 10 mm×12 mm were then elevated and removed exposing the underlying dura mater. The dura mater was incised bilaterally utilizing a micro-dissection blade and two circular dural defects each approximately 8 mm×10 mm were created under microdissection.

Surgical Procedure: Dural Repair

Induced dural defects were subsequently repaired with either the collagen graft material or the fully resorbable non-biologic non-woven graft material (FIGS. 1A & 1B). The collagen graft material is a biologic, xenogenic graft material composed of type I collagen derived from bovine Achilles tendon. The collagen graft material is highly cross-linked resulting in a firm, woven, suturable implant material suitable for use in dural repair. The collagen graft material was provided sterile and stored at room temperature prior to use. The non-woven graft material is a fully-resorbable non-biologic graft material composed of electrospun poly (lactic-co-glycolic acid) and polydioxanone. It possesses a unique non-woven architecture resulting in a compliant, flexible, and suturable implant material indicated for use in the repair of the dura mater. The fully resorbable non-biologic non-woven graft material was provided sterile and stored at room temperature prior to use.

Prior to implantation, both graft materials were hydrated in sterile saline according to their respective instructions for use. Hydrated graft materials were then placed on the surgical field and trimmed to fit each dural defect. The size and shape of the graft material was selected to achieve at least a 2 mm overlap with the adjacent dura mater around the circumference of the defect. Hydrated grafts were then draped onto the dural defect to maximize contact between the graft material and the underlying dura and promote watertight closure. Graft materials were then secured to the native dura utilizing four interrupted, non-tension sutures (7-0 PDS) spaced equidistant around the circumference of the defect. Graft materials were implanted such that each animal received either two collagen graft material implants (n=5 animals) or two non-woven graft material implants (n=5 animals). Following repair of induced dural defects, each surgical site was irrigated and closed in two layers (periosteum/muscle, skin). Excised bone flaps were not replaced during closure.

Following surgery all animals were recovered prior to reintroduction into the general housing facility. Butorphanol was administered as a post-surgical analgesic in addition to the fentanyl transdermal patch. Post-operatively all animals were observed daily and evaluated weekly for behavioral signs of neurotoxicity (posture, pupillary light reflex, limb placement, proprioception reflex, corneal reflex, gait), indications of CSP leakage, and change in body weight.

Tissue Harvesting/CSP Evaluation

All animals were humanely euthanized 4 weeks post-operatively. CSP was collected for physiochemical analysis by inserting a needle into the cisterna magna and aspirating 1-2 ml of fluid which was then placed in cold-storage. Following CSP collection, the skull, brain, and implant sites were excised en bloc and fixed in neutral buffered formalin. Draining lymph nodes were similarly explanted and fixed in neutral buffered formalin. CSP fluid was sent Logan Regional Hospital (Logan, Utah) for physiochemical analysis. CSP was analyzed for cellular content (white blood cells, neutrophils, lymphocytes, monocytes/macrophages, eosinophils, basophils, lining cells, red blood cells) as well as glucose and protein levels.

Histological/Histopathological Analysis

Explanted skulls and peripheral lymph nodes were embedded in epoxy resin, blocked, and sectioned. Sections of the implant site (including neodural tissue and adjacent skull/brain) were stained with Luxol Fast Blue and Hematoxylin & Eosin (H&E) to visualize and evaluate the general health of neodural tissue, cortical tissue, and myelin. Sections of the implant site were also immunostained for Glial Fibrillary Acidic Protein (GFAP) to visualize local glial cells/astrocytes and evaluate the inflammatory response at the implant site. Sections of the lymph nodes were stained only with Hematoxylin & Eosin (H&E). Representative photomicrographs were then obtained utilizing light microscopy under a 40× optical objective and a Nanozoomer automated slide scanner provided by the Hope Center, Washington University School of Medicine.

The local tissue response to implanted dura substitute materials was quantified via microscopic scoring of neovascularization, vascularization of the tissue within the implant site, fibrosis, adhesions of the implant to the pia mater, and neoduralization. Fibrous capsule thickness (in μm) was averaged between three measurements in each implant site. If the presence of implant was not well defined, the thickness of fibrous tissue at the implant site was reported. Inflammation at the implant site was quantified by microscopically scoring the degree of infiltration of polymorphonuclear cells, lymphocytes, plasma cells, eosinophils, macrophages, and multinucleated giant cells into the implant field. Necrosis was scored as the severity of nuclear cellular debris from inflammatory cell death.

Results

Intraoperative/Postoperative Performance of Dura Substitute Materials

Both collagen biologic and non-biologic graft materials were successfully utilized to repair induced bilateral dural defects created in female New Zealand White rabbits. Intraoperative observations demonstrated that both commercially-available collagen-based grafts and fully-resorbable synthetic non-woven grafts possessed suitable properties for effective dural repair. Upon surgical implantation the non-woven graft material implants were noted to be less thick and more flexible/compliant than the collagen-based graft implants. The non-woven graft material implants were also observed to better conform to underlying native dura and were more easily sutured in place compared to the collagen-based graft implants.

Post-operatively all animals survived to the terminal time point and all animals exhibited normal behavior, neurological function and general health. Regular examination of the implant site confirmed that 0/10 implant sites containing the collagen-based graft implants and 0/10 implant sites containing The non-woven graft material exhibited signs of CSP leakage or focal implant site infection during the course of the study. Post-mortem examination of the repair sites further confirmed the absence of CSP leaks and pseudomeningocele in all animals on study. Post-operative observation demonstrated that both the non-woven graft material and the collagen-based graft implants were efficacious in repairing dural defects and preventing CSP leakage.

Analysis of Cerebrospinal Fluid/Sentinel Lymph Nodes

Cellular and physiochemical analysis of CSP collected from animals undergoing dural repair utilizing the collagen-based graft and the non-woven graft material was conducted in order to identify potential signs of neurotoxicity, inflammation, and/or infection resulting from implant materials. Complete blood counts and protein analysis conducted on collected CSP appeared normal in all animals implanted with both the collagen-based graft and the non-woven graft materials. Negative findings in CSP analysis suggest that neither implant material induced neurotoxic or inflammatory responses in regional cortical tissue. Histological analysis of sentinel lymph nodes was conducted in order to further examine the inflammatory and foreign body response to the dural substitute implants. Animals implanted with both the collagen-based graft and the non-woven graft materials exhibited normal appearing lymph nodes upon H&E staining suggesting no regional inflammatory or foreign body response to the grafts.

Histological/Histopathological Analysis of Implant Sites

Histological and histopathological analysis of surgical repair sites was conducted to qualitatively and quantitatively evaluate the efficacy of various dura substitute materials and the tissue/inflammatory response to the implanted grafts. Qualitative analysis of representative sections of defect sites repaired with either the collagen-based graft and the non-woven graft materials demonstrate significant differences in the efficacy of the implanted material (FIGS. 2A-2D). Coronal sections obtained from defect sites repaired with the collagen-based graft material demonstrated poor cellular infiltration and incorporation into the graft material. Sections further demonstrated frequent fibrous adhesions or connective tissue bridging the implanted the collagen-based graft material and the underlying cortical tissue. Qualitative observations further demonstrated frequent incomplete neoduralization across the cortical surface of the collagen-based graft material. In comparison, qualitative analysis of representative histological sections obtained from defect sites repaired with the fully-resorbable non-woven graft material demonstrated increased cellular infiltration and lower incidence of fibrous cortical adhesions. Coronal sections further demonstrated more complete neoduralization across the cortical surface of the non-woven graft material. Noted differences in tissue response to the implanted materials further related to the state of graft resorption at the time of explantation. At 4 weeks post-operatively, the collagen-based graft material demonstrated minimal cellular infiltration and resorption, while the non-woven graft material demonstrated marked cellular infiltration and resorption (FIGS. 2A-2D).

Figures 3A, 3B, 3C, 3D:
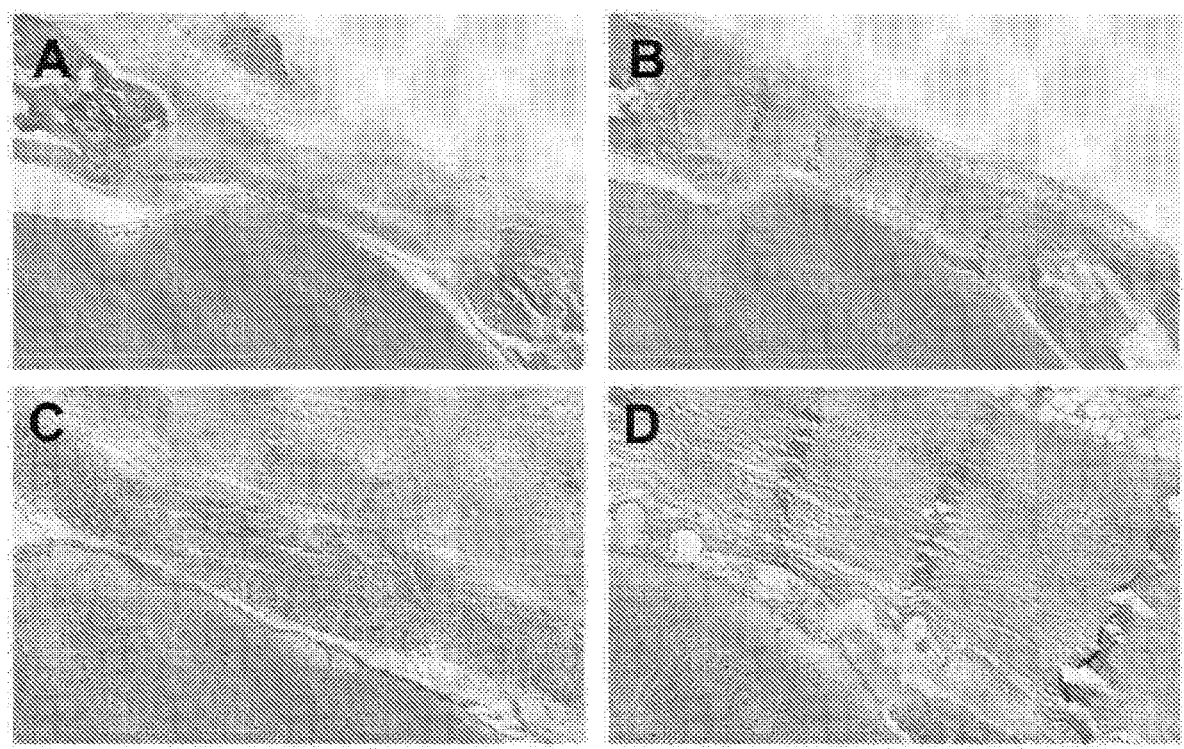
FIGS. 3A-3D are micrographic images depicting Hematoxylin & Eosin-stained sections obtained from defects repaired with a non-woven graft material of the present disclosure (FIGS. 3A & 3C) and a collagen graft material (FIGS. 3B & 3D) 4 weeks post-operatively.
Figure 4:
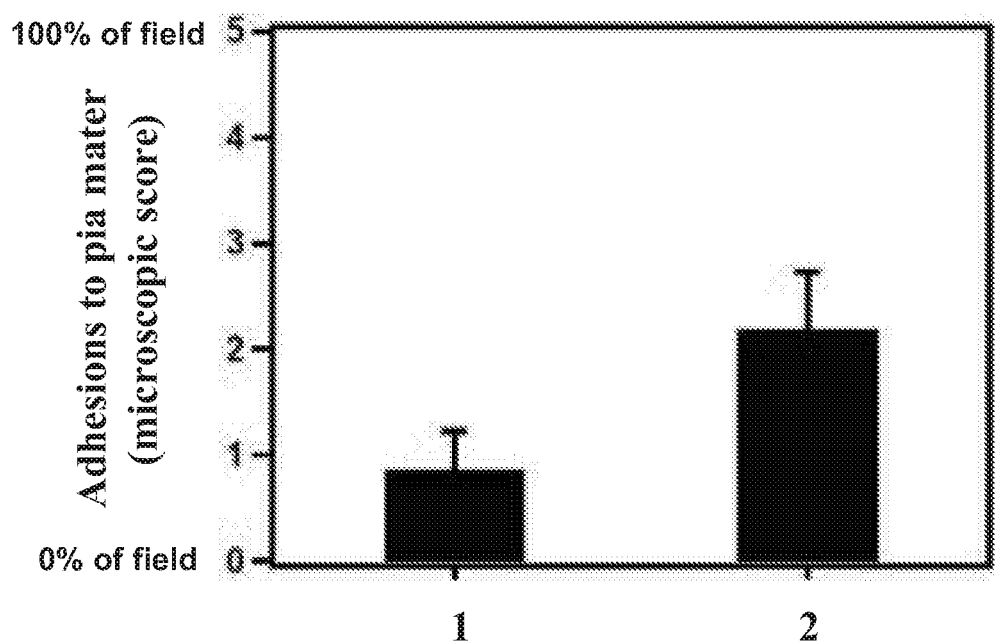
FIG. 4 is a graph depicting the quantitative comparison of adhesions to pia mater present in defect sites implanted with a non-woven graft material (bar 1) of the present disclosure and a collagen graft material (bar 2).
Figure 5:
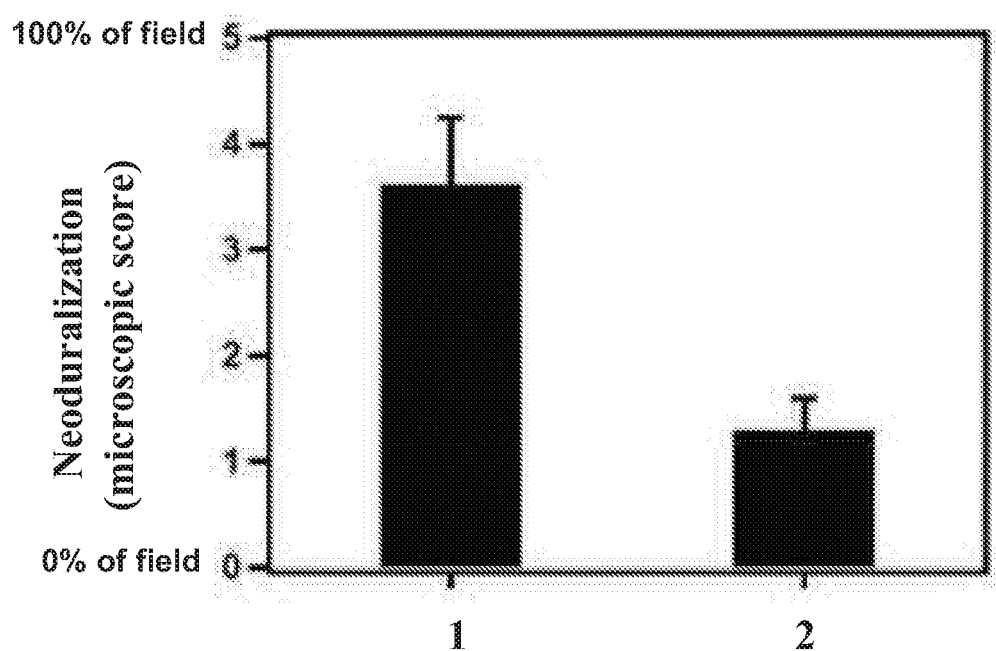
FIG. 5 is a graph depicting neoduralization present in defect sites implanted with a non-woven graft material of the present disclosure (bar 1) of the present disclosure and a collagen graft material (bar 2).
Figure 6:
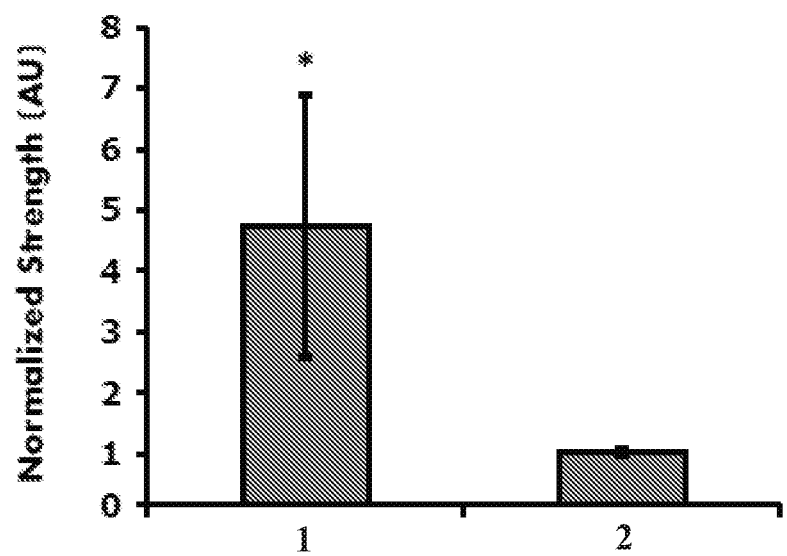
FIG. 6 is a graph depicting burst strength testing of the non-woven graft material (hydrated) of the present disclosure (bar 1) as compared to a collagen-based graft material (bar 2).
Figure 7:
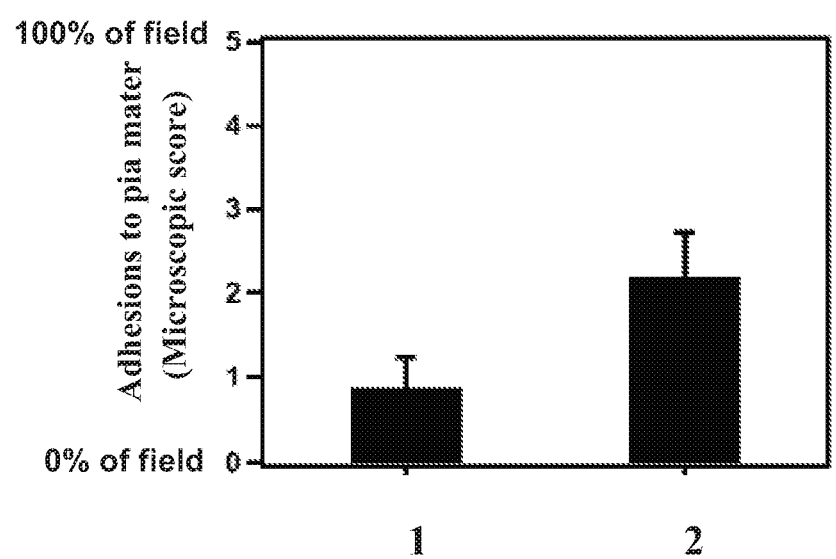
FIG. 7 is a graph depicting adhesions of the non-woven graft material of the present disclosure (bar 1) to pia mater as compared to adhesions of a collagen-based graft material (bar 2) to pia mater at 4 weeks post-operatively.
Figure 8:
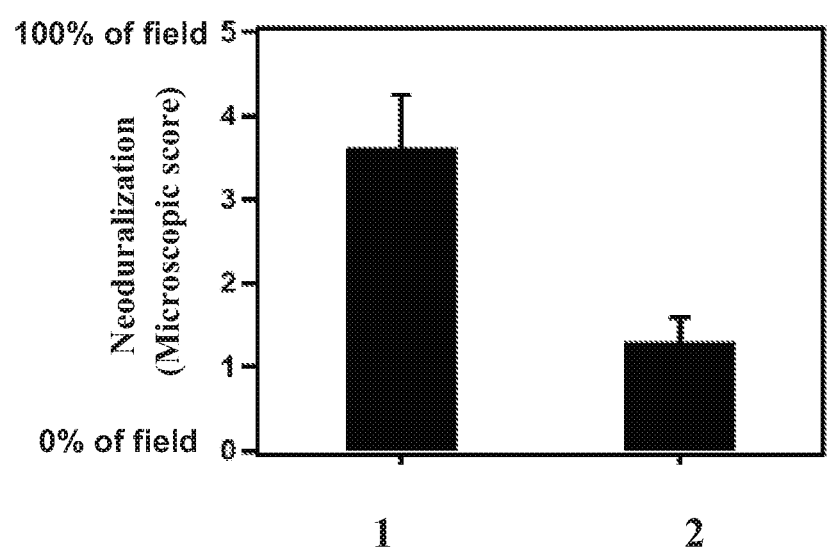
FIG. 8 is a graph depicting neoduralization to the non-woven graft material of the present disclosure (bar 1) as compared to neoduralization to a collagen-based graft material (bar 2) at 4 weeks post-operatively.

Quantitative scoring of histologic sections provided additional comparison of the tissue level reaction to both dura substitute devices. Microscopic scoring of histopathological examinations of the implant site revealed significant differences in the inflammatory and tissue-level responses to the non-woven graft material, as compared to the collagen-based graft material (FIGS. 3A & 3B and Table 1). The non-woven graft materials were observed to recruit a reduced number of inflammatory cells (e.g. monocytes and lymphocytes) compared to the collagen-based graft materials (see Table 1). The non-woven graft materials also exhibited less fibrosis and lower fibrous capsule thicknesses compared to the collagen-based graft material. Histopathological scoring of inflammation and tissue response further indicated that the non-woven graft material exhibited a lower inflammatory response, and was therefore classified as non-irritant, compared to the collagen-based graft material.

TABLE 1

Histopathological Evaluation

| | | Graft Material | |
|---|---|---|---|
| | | Non-woven Graft Material | Collagen-based Graft Material |
| Inflammation | Polymorphonuclear cells[a] | 0 | 0.8 |
| | Lymphoytes[a] | 0 | 0.9 |
| | Plasma cells[a] | 0 | 0.3 |
| | Eosinophils[a] | 0 | 0 |
| | Mast cells[a] | 0 | 0 |

TABLE 1-continued

Histopathological Evaluation

|  |  | Graft Material | |
| --- | --- | --- | --- |
|  |  | Non-woven Graft Material | Collagen-based Graft Material |
| Tissue Response | Macrophages[a] | 0.8 | 0.8 |
|  | Multinucleated giant cells[a] | 0.9 | 0 |
|  | Necrosis[b] | 0 | 0 |
|  | Neovascularization[c] | 1.0 | 1.0 |
|  | Implant vascularization[d] | 1.5 | 0.4 |
|  | Neoduralization[e] | 3.6 | 1.3 |
|  | Fibrosis[f] | 2.3 | 3.1 |
|  | Pia mater adhesions[e] | 0.9 | 2.2 |

[a]Scored from 0 (absent)-4 (packed).
[b]Scored from 0 (absent)-4 (severe).
[c]Scored from 0 (absent)-4 (extensive capillaries supported by fibroblasts).
[d]Scored from 0 (absent)-5 (>75% of implant field).
[e]Scored from 0 (absent)-5 (100% of implant field).
[f]Scored from 0 (no fibrous capsule)-4 (fibrous capsule > 300 um thick).

The results presented herein offer a comparative analysis of the non-woven graft material and the collagen-based graft material in a bilateral rabbit duraplasty model. Both materials demonstrated effective repair of induced dural defects and prevention of CSP leakage without damaging proximal neural tissue. This functional comparison demonstrates equivalent performance of the non-woven graft material with gold-standard collagen-matrices widely used in contemporary neurosurgical clinics. Histopathological analysis of the implant site 4 weeks post-operatively revealed, however, that the performance of the non-woven graft material and the collagen-based graft material were not equivalent when considering local inflammatory and tissue-level responses elicited at the site of implantation. The non-woven graft material exhibited distinct advantages in local tissue response including reduced fibrosis/fibrous capsule formation and decreased cortical adhesions compared to the collagen-based graft material (FIGS. 3A-3B). Furthermore, the non-woven graft material induced greater neoduralization than the collagen-based graft material at the implant site, and in some cases the non-woven graft material supported complete neoduralization of the defect by the time of explantation (FIG. 3C).

The difference in tissue response to the non-woven graft material and the collagen-based graft material is likely influenced by differences in the composition of the implants and, specifically, differences in the resorbable nature of the materials. The collagen-based graft material did not appear to undergo significant resorption 4 weeks after implantation, but rather was associated with minimal cellular/tissue infiltration and significant fibrous capsule around the acellular, crosslinked collagen material. Thus, although the collagen-based graft material is composed of biologically-derived animal-based collagen, the biological response to the implanted material is unlike what may be expected of native protein. The collagen-based graft material, despite its biologic composition, exhibits an in vivo response significantly divergent to that of native or fresh tissue.

Alternatively, the non-woven graft material implant demonstrated modest resorption in parallel with increased cellular infiltration of the material. Particularly, resorbing elements of the non-woven graft material implant were observed to be localized within macrophages that had infiltrated the implant site. This observation confirms the resorbable and transient nature of the non-woven graft material. The synthetic electrospun material utilized in the construction of the non-woven graft material provided an environment in which cells could migrate and which could be broken down to allow subsequent remodeling of the tissue. Fully-resorbable constructs such as the non-woven graft material may possess multiple advantages over long-term or permanent implants in that the material serves as an acute barrier and scaffold for new tissue formation yet resorbs following tissue regeneration precluding undue chronic reactions to the implanted material. Furthermore, the lack of animal-derived, xenogenic, or allogenic constituents may effectively reduce the incidence of allergic or inflammatory responses to the implanted dura substitute material commonly associated with existing biologic graft materials.

The lack of resorption of the implanted the collagen-based graft material is likely an effect of the post-processing utilized in the construction of the biologic material. The crosslinking of bovine collagen required to provide the mechanical strength necessary for intraoperative use and suturability simultaneously affected the biologic and structural elements of the material. As demonstrated in this Example, fully-resorbable synthetic dura substitutes can provide adequate mechanical strength for suturability, optimal handling and compliance, as well as reliable resorption that encourages tissue remodeling in the form of neoduralization. The non-woven graft material is unique, however, in that the non-biologic dura substitute also exhibits reduced inflammation, decreased fibrosis, and fewer adhesions to the pia mater than gold-standard biologic dura substitutes presently in use in neurosurgical clinics. The non-woven architecture, created by electrospinning, may be attributed with an improved tissue response, as compared to alternative synthetic dura substitutes. Furthermore, this mechanism of synthesis provides a material with superior handling and drapability as compared to alternatives with reduced compliance. The non-woven graft materials (e.g., the non-woven graft material) of the present disclosure thereby offer a unique and attractive option in dural repair procedures that provides ease of handling, efficacy, and biocompatibility, ultimately leading to improved dural repair.

The non-woven graft materials of the present disclosure provide fully-resorbable, non-biologic dura substitutes that offer a unique combination of mechanical strength for suturability and compliance for ease of handling. The non-woven architecture of the materials permits cellular infiltration and supports full resorption of the implant material while encouraging regeneration of native dura. The materials effectively closed dura defects equivalent to a gold-standard biologic dura substitute (the collagen-based graft material) and induced a superior local tissue response characterized by decreased inflammation and increased neoduralization. The non-woven graft materials thereby offer significant advantages over existing dura substitutes that may lead to improved clinical outcomes in multiple neurosurgical settings.

Example 2

In this Example, the physical properties of the non-woven mesh were determined by direct measurements of mesh fiber, pore size, mass, and dimensions.

Test articles were cut into four portions of approximately 1 cm$^2$ each. Excised portions were attached to a standard 12 mm SEM stub using double sided carbon tape. Two portions were positioned in a "dimple up" orientation and two portions were positioned in a "dimple down" orientation. Samples were coated with −20 Å of gold using a Denton Desk V sputter coater. Physical properties analyzed were average pore size, average fiber diameter, average thickness, side dimension, mass, and "areal density" (g/m²). Dimensional data was collected by recording a series of secondary electron micrographs from each sample using a TESCAN Vega 3 scanning electron microscope. A magnification level of 2 k× was specified for data collection. Images were also collected at 500× magnification. Physical properties were measured directly on the micrographs using calibrated software embedded in the TESCAN operating system. The number of properties recorded per micrograph were 30 fibers per image and 20 pores per image. Fiber and pore locations were randomly selected. Mean thickness was determined by averaging five measurements from a 100× cross section field of view. Side dimension was measured with a calibrated ruler traceable to NIST standards. Mass was determined by weighing samples on a calibrated analytical balance before cutting.

Example 3

In this Example, the non-destructive testing was conducted on non-woven material of the disclosure.

Mass was determined by weighing the sample on a balance. Size was measured to include the length and width of the material using calibrated calipers. Area (cm²) was calculated. "Areal density" (g/m²) was calculated using mass and size measurements.

Example 4

In this Example, the tensile strength on non-woven material of the disclosure was analyzed.

Specifically the tensile strength of 1 inch×3 inch strips prepared from a 3 inch×3 inch non-woven graft material sample at break and % elongation at break was performed using an Instron Tester. A 1 inch×3 inch strip was placed into the grips of the Instron Tester. Location of the break, gauge length, grip separation speed, sample and specification identification, specimen size parameters and preconditioning parameters were noted. Tensile strength was measured in Newtons (N) and the % elongation at break was measured in %.

Example 5

In this Example, the "suture pull-out" or the force required to pull out a suture from non-woven material of the disclosure was analyzed.

The force required to pull out a suture from non-woven material of the disclosure was analyzed using an Instron Tester on 1 inch×3 inch strips prepared from a 3 inch×3 inch non-woven graft material sample. Strips were soaked for 2 hours at room temperature in de-ionized water. Gauge length was set to 100.8 mm and the grip separation speed was set at 75 mm/minute. A 2-0 polypropylene monofilament suture was threaded through the center of the strip approximately 7.5 mm from the upper edge of the sample. Suture ends were clamped. Tearing of the sample was noted and data excluded suture breakage. The maximum pull-out force was measured in Newtons (N).

This materials and methods disclosed herein provide substitute materials for tissue repair. In particular, the materials and methods disclosed herein provide a non-biological substitute for tissue repair.

What is claimed is:

1. A bioabsorbable non-woven graft material for facilitating regeneration of tissue, the bioabsorbable non-woven graft material consisting of:
   a single non-woven electrospun polymeric scaffold, the non-woven electrospun polymeric scaffold formed by a first set of non-woven electrospun polymeric fibers and a second set of non-woven electrospun polymeric fibers, wherein the first set of non-woven electrospun polymeric fibers and the second set of non-woven electrospun polymeric fibers are commingled in the non-woven electrospun polymeric scaffold to form an architecture resembling a native extracellular matrix,
   the first set of non-woven electrospun polymeric fibers formed by depositing via electrospinning a first polymer composition comprising poly(glycolic) acid, the second set of non-woven electrospun polymeric fibers formed by depositing via electrospinning a second polymer composition comprising poly(lactide-co-caprolactone), the first polymer composition and the second polymer composition comprising different compositions;
   the non-woven electrospun polymeric scaffold further comprising a plurality of pores formed among the first set of non-woven electrospun polymeric fibers and the second set of non-woven electrospun polymeric fibers;
   the non-woven electrospun polymeric scaffold further comprising a top surface and a bottom surface, the top surface and the bottom surface comprising one or more different physical properties, wherein the one or more different physical properties comprise average fiber diameter;
   the non-woven electrospun polymeric scaffold comprising sufficient flexibility for applying the bioabsorable non-woven graft material to tissue, the non-woven electrospun polymeric scaffold comprising sufficient mechanical strength for the bioabsorbable non-woven graft material to be suturable, and the non-woven electrospun polymeric scaffold comprising sufficient mechanical strength for the bioabsorble non-woven graft material to be trimmable,
   wherein the bioabsorbable non-woven graft material is configured to facilitate regeneration of tissue.

2. The bioabsorbable non-woven graft material of claim 1, wherein the first set of non-woven electrospun polymeric fibers and the second set of non-woven electrospun polymeric fibers are substantially uniformly distributed throughout the non-woven electrospun polymeric scaffold.

3. The bioabsorbable non-woven graft material of claim 1, wherein the first set of non-woven electrospun polymeric fibers and the second set of non-woven electrospun polymeric fibers comprise an average diameter not greater than 2,000 nanometers.

4. The bioabsorbable non-woven graft material of claim 1, further comprising a plurality of protrusions arising from the top or bottom surface of the non-woven electrospun polymeric scaffold and a plurality of depressions in the top or bottom surface of the non-woven electrospun polymeric scaffold.

5. The bioabsorbable non-woven graft material of claim 4, wherein the plurality of protrusions and the plurality of depressions form a pattern on the surface of the non-woven electrospun polymeric scaffold.

6. The bioabsorbable non-woven graft material of claim 4, wherein one or more of the plurality of protrusions or the plurality of depressions are randomly distributed.

7. The bioabsorbable non-woven graft material of claim 4, wherein the plurality of protrusions comprise a substantially uniform height.

8. The bioabsorbable non-woven graft material of claim 4, wherein the plurality of depressions comprise a substantially uniform depth.

9. The bioabsorbable non-woven graft material of claim 1, wherein the tissue comprises skin or tendon, and the bioabsorbable non-woven graft material is adapted to repair or augment the skin or tendon.

10. The bioabsorbable non-woven graft material of claim 1, wherein the bioabsorbable non-woven graft material comprises a suture pull-out strength, the suture pull-out strength ranging from 1 Newtons to about 5 Newtons of force required for one or more sutures to be torn from bioabsorbable non-woven graft material.

11. The bioabsorbable non-woven graft material of claim 1, wherein the non-woven electrospun polymeric scaffold comprises interconnecting pores.

12. The bioabsorbable non-woven graft material of claim 1, wherein the non-woven electrospun polymeric scaffold comprises a surface pattern.

13. The bioabsorbable non-woven graft material of claim 12, wherein the surface pattern comprises a repeating non-random pattern.

14. The bioabsorbable non-woven graft material of claim 1, wherein a mean size of the plurality of pores is less than 300 micrometers squared.

15. A bioabsorbable non-woven graft material for facilitating regeneration of tissue, the bioabsorbable non-woven graft material consisting of:
  a single non-woven electrospun polymeric scaffold, the non-woven electrospun polymeric scaffold formed by a first set of non-woven electrospun polymeric fibers and a second set of non-woven electrospun polymeric fibers, wherein the first set of non-woven electrospun polymeric fibers and the second set of non-woven electrospun polymeric fibers are commingled in the non-woven electrospun polymeric scaffold,
  the first set of non-woven electrospun polymeric fibers formed by depositing via electrospinning a first polymer composition comprising glycolic acid, the second set of non-woven electrospun polymeric fibers formed by depositing via electrospinning a second polymer composition, the first polymer composition and the second polymer composition comprising different compositions;
  the non-woven electrospun polymeric scaffold further comprising a plurality of pores formed by the first set of non-woven electrospun polymeric fibers and the second set of non-woven electrospun polymeric fibers;
  the non-woven electrospun polymeric scaffold further comprising a top surface and a bottom surface comprising one or more different physical properties, wherein the one or more different physical properties comprise areal density;
  the non-woven electrospun polymeric scaffold comprising sufficient flexibility for applying the bioabsorable non-woven graft material to tissue, and the non-woven electrospun polymeric scaffold comprising sufficient mechanical strength for the bioabsorble non-woven graft material to be trimmable,
  wherein the bioabsorbable non-woven graft material is configured to facilitate regeneration of tissue.

16. The bioabsorbable non-woven graft material of claim 15, wherein the first set of non-woven electrospun polymeric fibers and the second set of non-woven electrospun polymeric fibers are substantially uniformly distributed throughout the bioabsorbable non-woven graft material.

17. The bioabsorbable non-woven graft material of claim 15, wherein the first set of non-woven electrospun polymeric fibers and the second set of non-woven electrospun polymeric fibers comprise an average diameter not greater than 2,000 nanometers.

18. The bioabsorbable non-woven graft material of claim 15, further comprising a plurality of protrusions arising from the top or bottom surface of the non-woven electrospun polymeric scaffold and a plurality of depressions in the top or bottom surface of the non-woven electrospun polymeric scaffold.

19. The bioabsorbable non-woven graft material of claim 18, wherein one or more of the plurality of protrusions or the plurality of depressions form a pattern.

20. The bioabsorbable non-woven graft material of claim 18, wherein the plurality of protrusions comprise a substantially uniform height.

21. The bioabsorbable non-woven graft material of claim 18, wherein one or more of the plurality of protrusions or the plurality of depressions are randomly distributed.

22. The bioabsorbable non-woven graft material of claim 15, wherein the first polymer composition comprises poly (glycolic) acid, and wherein the second polymer composition comprises poly(lactide-co-caprolactone).

23. The bioabsorbable non-woven graft material of claim 15, wherein the first polymer composition comprises poly (lactide-co-glycolide), and wherein the second polymer composition comprises polydioxanone.

24. The bioabsorbable non-woven graft material of claim 15, wherein the bioabsorbable non-woven graft material comprises a suture pull-out strength, the suture pull-out strength ranging from 1 Newtons to about 5 Newtons of force required for one or more sutures to be torn from bioabsorbable non-woven graft material.

25. A bioabsorbable non-woven graft material for facilitating regeneration of tissue, the bioabsorbable non-woven graft material consisting of:
  a single non-woven electrospun polymeric scaffold, the non-woven electrospun polymeric scaffold formed by a first set of non-woven electrospun polymeric fibers and a second set of non-woven electrospun polymeric fibers interlaid in the non-woven electrospun polymeric scaffold,
  the first set of non-woven electrospun polymeric fibers formed by depositing via electrospinning a first polymer composition comprising glycolic acid, the second set of non-woven electrospun polymeric fibers formed by depositing via electrospinning a second polymer composition, the first polymer composition and the second polymer composition comprising different compositions;
  the non-woven electrospun polymeric scaffold further comprising a plurality of pores formed among the first set of non-woven electrospun polymeric fibers and the second set of non-woven electrospun polymeric fibers;
  the non-woven electrospun polymeric scaffold further comprising a top surface and a bottom surface, the top surface and the bottom surface comprising one or more different physical properties, wherein the one or more different physical properties comprise average fiber density;
  the non-woven electrospun polymeric scaffold comprising sufficient flexibility for applying the bioabsorable non-woven graft material to tissue, and the non-woven electrospun polymeric scaffold comprising sufficient mechanical strength for the bioabsorbable non-woven graft material to be suturable;

wherein the bioabsorbable non-woven graft material is configured to facilitate regeneration of tissue.

26. The bioabsorbable non-woven graft material of claim 25, wherein the non-woven electrospun polymeric scaffold comprises a surface pattern.

27. The bioabsorbable non-woven graft material of claim 25, further comprising a plurality of protrusions arising from the top or bottom surface of the non-woven electrospun polymeric scaffold and a plurality of depressions in the top or bottom surface of the non-woven electrospun polymeric scaffold.

28. The bioabsorbable non-woven graft material of claim 25, wherein the first polymer composition comprises poly(glycolic) acid, and wherein the second polymer composition comprises poly(lactide-co-caprolactone).

29. The bioabsorbable non-woven graft material of claim 25, wherein the first polymer composition comprises poly(lactide-co-glycolide), and wherein the second polymer composition comprises polydioxanone.

30. The bioabsorbable non-woven graft material of claim 25, wherein the first set of non-woven electrospun polymeric fibers and the second set of non-woven electrospun polymeric fibers comprise an average diameter not greater than 2,000 nanometers.

* * * * *

UNITED STATES PATENT AND TRADEMARK OFFICE
CERTIFICATE OF CORRECTION

PATENT NO. : 11,224,677 B2
APPLICATION NO. : 17/226384
DATED : January 18, 2022
INVENTOR(S) : MacEwan It is certified that error appears in the above-identified patent and that said Letters Patent is hereby corrected as shown below:

On the Title Page

Page 4, Column 1 (item (56) Other Publications), Line 14, delete "Biocompalibility" and insert --Biocompatibility--.

Page 4, Column 1 (item (56) Other Publications), Line 24, delete "chitosa" and insert --chitosan--.

Page 4, Column 1 (item (56) Other Publications), Line 28, delete "Polmer" and insert --Polymer--.

Page 4, Column 1 (item (56) Other Publications), Line 28, delete "Enginering" and insert --Engineering--.

Page 4, Column 2 (item (56) Other Publications), Line 5, delete "fortissue" and insert --for tissue--.

Page 4, Column 2 (item (56) Other Publications), Line 20, delete "compsite artifical" and insert --composite artificial--.

Page 4, Column 2 (item (56) Other Publications), Line 53, delete "AlChE" and insert --AIChE--.

Page 5, Column 1 (item (56) Other Publications), Line 11, delete "(s" and insert --(ε--.

Page 5, Column 1 (item (56) Other Publications), Line 51, delete "tussie" and insert --tissue--.

Page 5, Column 1 (item (56) Other Publications), Line 58, delete "absorable" and insert --absorbable--.

Page 5, Column 1 (item (56) Other Publications), Line 58, delete "reinforeced" and insert --reinforced--.

Page 5, Column 1 (item (56) Other Publications), Line 69, delete "DermaMalrixand" and insert Signed and Sealed this
Tenth Day of May, 2022

Katherine Kelly Vidal
*Director of the United States Patent and Trademark Office*

--DermaMatrix and--.

Page 5, Column 1 (item (56) Other Publications), Line 69, delete "repopulaled" and insert --repopulated--.

Page 5, Column 2 (item (56) Other Publications), Line 13, delete "Applicalion," and insert --Application,--.

Page 5, Column 2 (item (56) Other Publications), Line 24, delete "10.1021/bm302000n)." and insert --10.1021/bm302000n.--.

Page 5, Column 2 (item (56) Other Publications), Line 45, delete "10.1021/la303490x)." and insert --10.1021/la303490x.--.

Page 5, Column 2 (item (56) Other Publications), Line 58, delete "nanofibres," and insert --nanofibers,--.

Page 5, Column 2 (item (56) Other Publications), Line 60, delete "Driplets" and insert --Droplets--.

Page 6, Column 1 (item (56) Other Publications), Line 17, delete "Scafforlds" and insert --Scaffolds--.

Page 6, Column 1 (item (56) Other Publications), Line 18, delete "Elactrostatic" and insert --Electrostatic--.

In the Specification

Column 1, Line 54, delete "facia" and insert --fascia--.

Column 4, Line 6 (approx.), below "BRIEF DESCRIPTION OF THE DRAWINGS" insert --The patent or application file contains at least one drawing executed in color. Copies of this patent or patent application publication with color drawing(s) will be provided by the Office upon request and payment of the necessary fee.--.

Column 7, Line 36, delete "aminocapronic" and insert --aminocaproic--.

Column 16, Line 63 (approx.), delete "Lymphoytesa" and insert --Lymphocytesa--.

In the Claims

Column 20, Line 35, In Claim 1, delete "bioabsorable" and insert --bioabsorbable--.

Column 20, Line 41, In Claim 1, delete "bioabsorble" and insert --bioabsorbable--.

Column 21, Line 58, In Claim 15, delete "bioabsorable" and insert --bioabsorbable--.

CERTIFICATE OF CORRECTION (continued)
U.S. Pat. No. 11,224,677 B2

Column 21, Line 61, In Claim 15, delete "bioabsorble" and insert --bioabsorbable--.

Column 22, Line 65, In Claim 25, delete "bioabsorable" and insert --bioabsorbable--.